United States Patent
Aram et al.

(10) Patent No.: US 9,131,945 B2
(45) Date of Patent: Sep. 15, 2015

(54) CUSTOMIZED PATIENT-SPECIFIC REVISION SURGICAL INSTRUMENTS AND METHOD

(71) Applicant: DEPUY SYNTHES PRODUCTS, INC., Raynham, MA (US)

(72) Inventors: Luke J. Aram, Warsaw, IN (US); Janelle M. Lubensky, Winona Lake, IN (US); Rebecca L. Chaney, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 164 days.

(21) Appl. No.: 13/793,407

(22) Filed: Mar. 11, 2013

(65) Prior Publication Data

US 2014/0257309 A1    Sep. 11, 2014

(51) Int. Cl.
*A61B 17/17* (2006.01)
*A61B 17/15* (2006.01)
*A61B 19/00* (2006.01)
*A61F 2/38* (2006.01)
*A61F 2/30* (2006.01)
*A61B 17/56* (2006.01)

(52) U.S. Cl.
CPC ............. *A61B 17/154* (2013.01); *A61B 17/155* (2013.01); *A61B 17/157* (2013.01); *A61B 17/1764* (2013.01); *A61B 19/50* (2013.01); *A61F 2/3859* (2013.01); *A61B 2017/568* (2013.01); *A61F 2/30942* (2013.01); *A61F 2002/3069* (2013.01)

(58) Field of Classification Search
CPC .................... A61B 17/1764; A61B 2017/568; A61B 2/30942
See application file for complete search history.

(56) References Cited

U.S. PATENT DOCUMENTS

| 5,133,660 A | 7/1992 | Fenick |
| 5,320,529 A | 6/1994 | Pompa |

(Continued)

FOREIGN PATENT DOCUMENTS

| EP | 0645984 | 12/1993 |
| EP | 0756735 | 10/1995 |

(Continued)

OTHER PUBLICATIONS

Radermacher et al., "Computer Assisted Orthopaedic Surgery With Image Based Individual Templates", Clin Orthopaedics and Related Research (354), Sep. 1998, pp. 28-38.

(Continued)

*Primary Examiner* — Andrew Yang
(74) *Attorney, Agent, or Firm* — Barnes & Thornburg LLP

(57) ABSTRACT

A surgical instrument including a customized patient-specific guide block is disclosed. The customized patient-specific guide block includes a first surface, a bone-facing surface, a second surface positioned opposite the first surface and the bone-facing surface, and a guide pin hole extending between the second surface and the bone-facing surface. The first surface has a customized prosthesis-specific negative contour shaped to match a corresponding contour of a prosthetic component, and the customized prosthesis-specific negative contour includes a concave surface shaped to match a convex surface of the corresponding contour of the prosthetic component. A method of performing an orthopaedic surgical procedure is also disclosed.

10 Claims, 33 Drawing Sheets

(56) References Cited

U.S. PATENT DOCUMENTS

| | | | |
|---|---|---|---|
| 5,768,134 | A | 6/1998 | Swaelens et al. |
| 5,824,085 | A | 10/1998 | Sahay et al. |
| 6,327,491 | B1 | 12/2001 | Franklin et al. |
| 2002/0007294 | A1 | 1/2002 | Bradbury et al. |
| 2008/0161815 | A1 | 7/2008 | Schoenefeld et al. |
| 2010/0212138 | A1 | 8/2010 | Carroll et al. |

FOREIGN PATENT DOCUMENTS

| | | |
|---|---|---|
| WO | 93/25157 A1 | 12/1993 |
| WO | 95/28688 A1 | 10/1995 |
| WO | 2012024306 | 2/2012 |
| WO | 2012024306 A1 | 2/2012 |
| WO | 2012176077 | 12/2012 |
| WO | 2012176077 A1 | 12/2012 |
| WO | 2013025814 | 2/2013 |
| WO | 2013025814 A1 | 2/2013 |

OTHER PUBLICATIONS

Hafez et al., "Computer-assisted Total Knee Arthoplasty Using Patient-specific Templating", Clin Orthopaedics and related research (444), Mar. 2006, pp. 184-192.
PCT International Search Report and Written Opinion, International Application No. PCT/US2014/018004, May 17, 2014, 7 pages.
Berry, Seedhom, et al., "Personalised image-based templates for intra-operative guidance," Proceedings of the Institution of Mechanical Engineers, Part H: Journal of Engineering in Medicine, 111-118, 2005.
Radermacher et al., "Computer-Integrated Orthopaedic Surgery: Connection of Planning and Execution in Surgical Intervention," Computer Integrated Surgery, 451-463, 1995.
Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P Nolte and R. Ganz, eds, 42-52, Hogrefe & Huber Publishing 1999.
European Search Report; European Patent Application No. 08165418.8-2165; dated Jan. 23, 2009; 6 pages.
Hube et al.; Orthopaedic Surgery the Essentials, Chaper 36 Knee Reconstruction; 1999; 12 pages.
Corin Medical Limited; The Corin X-ActTM Instrumentation and Operative Technique; Nov. 1998; 9 pages.
Kraus et al.; A Comparative Assessment of Alignment Angle of the Knee by Radiographic and Physical Examination Methods; Jun. 6, 2005; 6 pages.
Depuy; LCS Total Knee System—Surgical Procedure; 1989; 36 pages.
Engh et al.; Legent II Surgical Technique; The Concept of Personalization—Total Knee Replacement Using the AMK—Legend II; 1992; 31 pages.
Lotke; Knee Arthroplasty; Primary Total Knees—Standard Principles and Techniques; Raven Press, Ltd.; 5 pages; 1995.
Mills et al.; Use of Computer Tomographic Reconstruction in Planning Osteotomies of the Hip; Jan. 1992; 6 pages.
Portheine et al.; Development of a clinical demonstrator for computer assisted orthopedic surgery with CT-image based individual templates; 1997; 6 pages.
Radermacher et al.; Image Guided Orthopedic Surgery Using Individual Templates; 10 pages.
"The Vision and Reality of Wearable Computing", XP-002399700, Apr. 1, 2004, 3 pages.
Sharma et al.; The Role of Knee Alignment in Disease Progression and Functional Decline in Knee Osteoarthritis; Jul. 11, 2001; American Medical Association; 10 pages.
Accuracy of CT-Based Patient Specific Total Knee Arthroplasty Instruments; AAHKS 20th Annual Meeting, Submission Record, Submission ID # 4177, Apr. 14, 2010.
PCT Search Report for Application PCT/US2008/078143, Dec. 18, 2008, 17 pages.
Talbot et al., "A home-based pedometer-driven walking program to increase physical actifvity in order adults with osteoarthritis of the knee: a preliminary study," Journal of the American Geriatrics Society, vol. 51, No. 3, 2003, 6 pages.
"Measuring functional abilities of patients with knee problems; rationale and construction of the DynaPort knee test," Knee Surgery, Sports Traumatology, Arthroscopy, vol. 10, Mar. 2002, pp. 204-212.
"Automated physical activity monitoring: validation and comparison with physiological and self-report measures," Psychophysiology, vol. 30, 1993, pp. 296-305.
European Search Report for European Patent Application No. 10150487.6-2310, May 12, 2010, 6 pages.
European Search Report for European Patent Application No. 09171188.7-2310, Sep. 24, 2010, 7 pages.
Chinese First Office Action, Chinese Patent Application No. 200880118434.4, Sep. 7, 2011, 12 pages.
International Search Report & Written Opinion of the International Searching Authority, Int'l. Appl. No. PCT/US2014/018004, dated May 27, 2014, 14 pages.

CUSTOMIZED PATIENT-SPECIFIC REVISION SURGICAL INSTRUMENTS AND METHOD

The present disclosure relates generally to customized orthopaedic surgical instruments, and in particular to surgical instruments that have been customized to interface with specific prostheses and patients.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis, sometimes called a "primary knee prosthesis," is surgically removed and a replacement or revision knee prosthesis is implanted. In some revision knee surgeries, all of the components of the primary knee prosthesis, including, for example, the tibial tray, the femoral component, and the polymer bearing, may be surgically removed and replaced with revision prosthetic components. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, reamers, drill guides, prosthetic trials, and other surgical instruments to prepare the patient's bones to receive the knee prosthesis. Typically, the orthopaedic surgical instruments are generic with respect to the patient such that the same orthopaedic surgical instrument may be used on a number of different patients during similar orthopaedic surgical procedures.

SUMMARY

According to one aspect of the disclosure, a surgical instrument including a customized patient-specific guide block is disclosed. The customized patient-specific guide block includes a first surface, a bone-facing surface, a second surface positioned opposite the first surface and the bone-facing surface, and a guide pin hole extending between the second surface and the bone-facing surface. The first surface has a customized prosthesis-specific negative contour shaped to match a corresponding contour of a prosthetic component. The customized prosthesis-specific negative contour includes a concave surface shaped to match a convex surface of the corresponding contour of the prosthetic component.

In some embodiments, the bone-facing surface may include a lateral surface of the guide block, and the second surface may include a medial surface of the guide block. In some embodiments, the prosthetic component may be a femoral prosthetic component. The convex surface of the corresponding contour of the femoral prosthetic component may include a medial condyle surface, and the concave surface of the customized prosthesis-specific negative contour may include a medial concave surface.

Additionally, in some embodiments, the bone-facing surface may include a posterior surface of the guide block, and the second surface may include an anterior surface of the guide block.

In some embodiments, the bone-facing surface of the guide block may have a customized patient-specific negative contour shaped to match a corresponding bone contour of a femur of a patient. The customized patient-specific negative contour may include a unique plurality of depressions and ridges that match a corresponding plurality of ridges and depressions of the corresponding bone contour of the femur of the patient.

In some embodiments, the guide block further may include a substantially-planar cutting guide surface extending between the bone-facing surface and the second surface.

In some embodiments, the prosthetic component may be a tibial tray including a curved surface, and the convex surface of the corresponding contour of the tibial tray may include the curved surface. The concave surface of the customized prosthesis-specific negative contour may include a curved inner surface.

According to another aspect, a method of performing an orthopaedic surgical procedure is disclosed. The method includes aligning a customized patient-specific guide block with a first prosthetic component implanted in an end of a bone of a patient, attaching the customized patient-specific guide block to the first prosthetic component in a unique location and orientation on the end of the bone, and advancing a guide pin through a guide pin hole of the customized patient-specific guide block into the bone when the customized patient-specific guide block is positioned on the first prosthetic component. The method also includes detaching the customized patient-specific guide block from the first prosthetic component and the end of the bone while leaving the guide pin secured to the bone, removing the first prosthetic component from the end of the bone, engaging an alignment block with the guide pin to position a cutting block on the bone, and resecting the end of the bone using the cutting block to guide the resection.

In some embodiments, positioning the customized patient-specific guide block on the first prosthetic component in the unique location and orientation may include engaging a customized prosthesis-specific negative contour of the customized patient-specific guide block with a corresponding contour of the first prosthetic component. The customized prosthesis-specific negative contour may be shaped to match the corresponding contour of the first prosthetic component.

In some embodiments, the first prosthetic component may include a femoral prosthetic component having a pair of curved condyle surfaces configured to engage a bearing surface. Additionally, engaging the customized prosthesis-specific negative contour of the customized patient-specific guide block with the corresponding contour of the first prosthetic component may include engaging a concave surface of the customized patient-specific guide block with a medial condyle surface of the femoral prosthetic component.

In some embodiments, the method may include securing the alignment block to the cutting block and engaging the alignment block with the guide pin may include advancing the cutting block along an anatomical axis of the bone to advance the alignment block into contact with the guide pin.

In some embodiments, the alignment block may include an indicator of a target joint line of a second prosthetic component.

In some embodiments, the method may include assembling the customized patient-specific guide block by locking a first removable drill bushing into a first hole of a customized patient-specific pin guide, and locking a second removable drill bushing into a second hole of the customized patient-specific pin guide. In some embodiments, the cutting block may include a patient-universal cutting block having a distal cutting guide.

In some embodiments, engaging the alignment block with the guide pin to position the cutting block on the bone may include positioning the guide pin in a guide pin hole of the alignment block, advancing the alignment block into contact with the cutting block, engaging the cutting block with the bone, and aligning the cutting block with an indicator defined on the alignment block. The indicator may correspond to a target anterior-posterior position of the cutting block.

In some embodiments, the method may include advancing a bone saw along a cutting guide surface of the customized patient-specific guide block when the customized patient-specific guide block is positioned on the first prosthetic component. In some embodiments, attaching the customized patient-specific guide block to the first prosthetic component may include engaging a customized patient-specific negative contour shaped to match a corresponding contour of the bone of the patient with the bone of the patient. The customized patient-specific negative contour may include a unique plurality of depressions and ridges that match a corresponding plurality of ridges and depressions of the corresponding contour of the bone of the patient.

According to another aspect, a method of fabricating a customized patient-specific guide block is disclosed. The method includes generating a image of a patient's bony anatomy and an implanted prosthetic component secured to the patient's bony anatomy, identifying landmarks on the patient's bony anatomy and the prosthetic component, selecting a revision surgical instrument based the image and the landmarks, and manufacturing the customized patient-specific guide block including a customized prosthesis-specific negative contour shaped to match a corresponding contour of the implanted prosthetic component. The customized prosthesis-specific negative contour includes a concave surface shaped to match a convex surface of the corresponding contour of the implanted prosthetic component.

In some embodiments, selecting the revision surgical instrument may include generating a second image showing a planned position of the revision surgical instrument relative the patient's bony anatomy.

In some embodiments, the method may include manufacturing a second customized patient-specific guide block based on the planned position of the revision surgical instrument. The second customized patient-specific guide block may include an indicator of the planned position.

In some embodiments, the method may include selecting a revision orthopaedic prosthesis based the image and the landmarks. Additionally, selecting the revision orthopaedic prosthesis may include selecting a first revision orthopaedic prosthesis from a plurality of revision orthopaedic sprostheses, overlaying a digital template of the first revision orthopaedic prosthesis on the image to create a second image showing the first revision orthopaedic prosthesis implanted in the patient's bone, and selecting a second revision orthopaedic prosthesis from the plurality of revision orthopaedic prostheses based on the second image.

BRIEF DESCRIPTION OF THE DRAWINGS

The detailed description particularly refers to the following figures, in which.

DETAILED DESCRIPTION OF THE DRAWINGS

Figure 1:
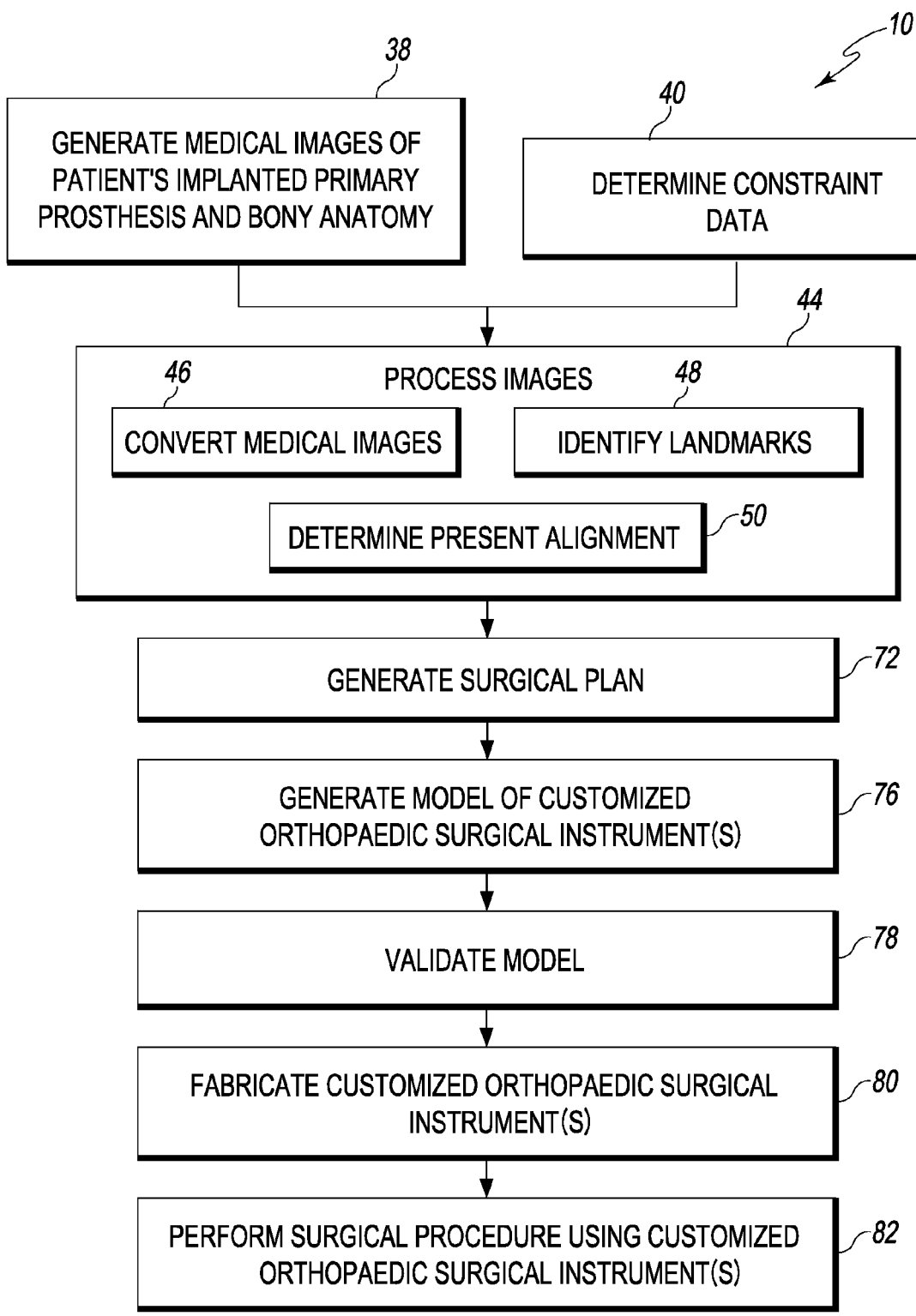
FIG. 1 is a simplified flow diagram of an algorithm for designing and fabricating a customized patient-specific orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting guide blocks, customized patient-specific femoral cutting guide blocks, and customized patient-specific alignment guides.

In some embodiments, the customized patient-specific orthopaedic surgical instrument may be configured to interface with a patient-universal instrument to position the patient-universal instrument in a preplanned location relative to the bone or bones of the patient. The customized patient-specific orthopaedic surgical instrument may also be customized to the particular patient based on the location at which the instrument is to be coupled to one or more bones of the patient, such as the femur and/or tibia. For example, in some embodiments, the customized patient-specific orthopaedic surgical instrument may include a bone-contacting or facing surface having a negative contour that matches or substantially matches the contour of a portion of the relevant bone of the patient. As such, the customized patient-specific orthopaedic surgical instrument is configured to be coupled to the bone of a patient in a unique location and position with respect to the patient's bone. That is, the negative contour of the bone-contacting surface is configured to receive the matching contour surface of the portion of the patient's bone to position the customized patient-specific orthopaedic surgical instrument at the unique location and position with respect to the patient's bone.

In revision surgical procedures in which the previously implanted or primary prosthesis is surgically removed and a replacement prosthesis is implanted, the customized patient-specific orthopaedic surgical instrument may be customized to engage the primary prosthesis before it is removed to position the instrument in a unique location and position relative to one or more bones of the patient. In such embodiments, the customized patient-specific orthopaedic surgical instrument may include a prosthesis-engaging or contacting surface having a negative contour that matches or substantially matches the contour of a portion of the implanted primary prosthesis. That is, the negative contour of the prosthesis-engaging surface is configured to receive the matching contour surface of the portion of the implanted primary prosthesis to position the customized patient-specific orthopaedic surgical instrument at a unique location and position with respect to the primary prosthesis and thus the patient's bone. Because the customized patient-specific orthopaedic surgical instrument is configured to be coupled to the previously implanted prosthesis and patient's bone in the unique location and position, the orthopaedic surgeon's guesswork and/or intra-operative decision-making with respect to the placement of the orthopaedic surgical instrument are reduced.

For example, the orthopaedic surgeon may not be required to locate landmarks of the patient's bone to facilitate the placement of the orthopaedic surgical instrument, which typically requires some amount of estimation on part of the surgeon. Rather, the orthopaedic surgeon may simply couple the customized patient-specific orthopaedic surgical instrument on the implanted primary prosthesis and bone or bones of the patient in the unique location. When so coupled, the cutting plane, drilling/pinning holes, milling holes, and/or other guides are defined in the proper location relative to the bone and intended orthopaedic prosthesis. The customized patient-specific orthopaedic surgical instrument may be embodied as any type of orthopaedic surgical instrument such as, for example, a bone-cutting block, a drilling/pin guide, a milling guide, or other type of orthopaedic surgical instrument configured to be coupled to a bone and/or the implanted primary prosthesis of a patient.

It should also be appreciated that in some embodiments the customized patient-specific orthopaedic surgical instrument may include both a prosthesis-engaging or contacting surface having a negative contour matching or substantially matching the contour of a portion of the implanted primary prosthesis and a bone-contacting or facing surface having a negative contour matching or substantially matching the contour of a portion of the relevant bone of the patient. In such embodiments, the negative contour of the prosthesis-engaging surface is configured to receive the matching contour surface of the portion of the implanted primary prosthesis and the negative contour of the bone-contacting surface is configured to receive the matching contour surface of the portion of the patient's bone to position the customized patient-specific orthopaedic surgical instrument at a unique location and position with respect to the implanted primary prosthesis and the patient's bone.

Figure 2:
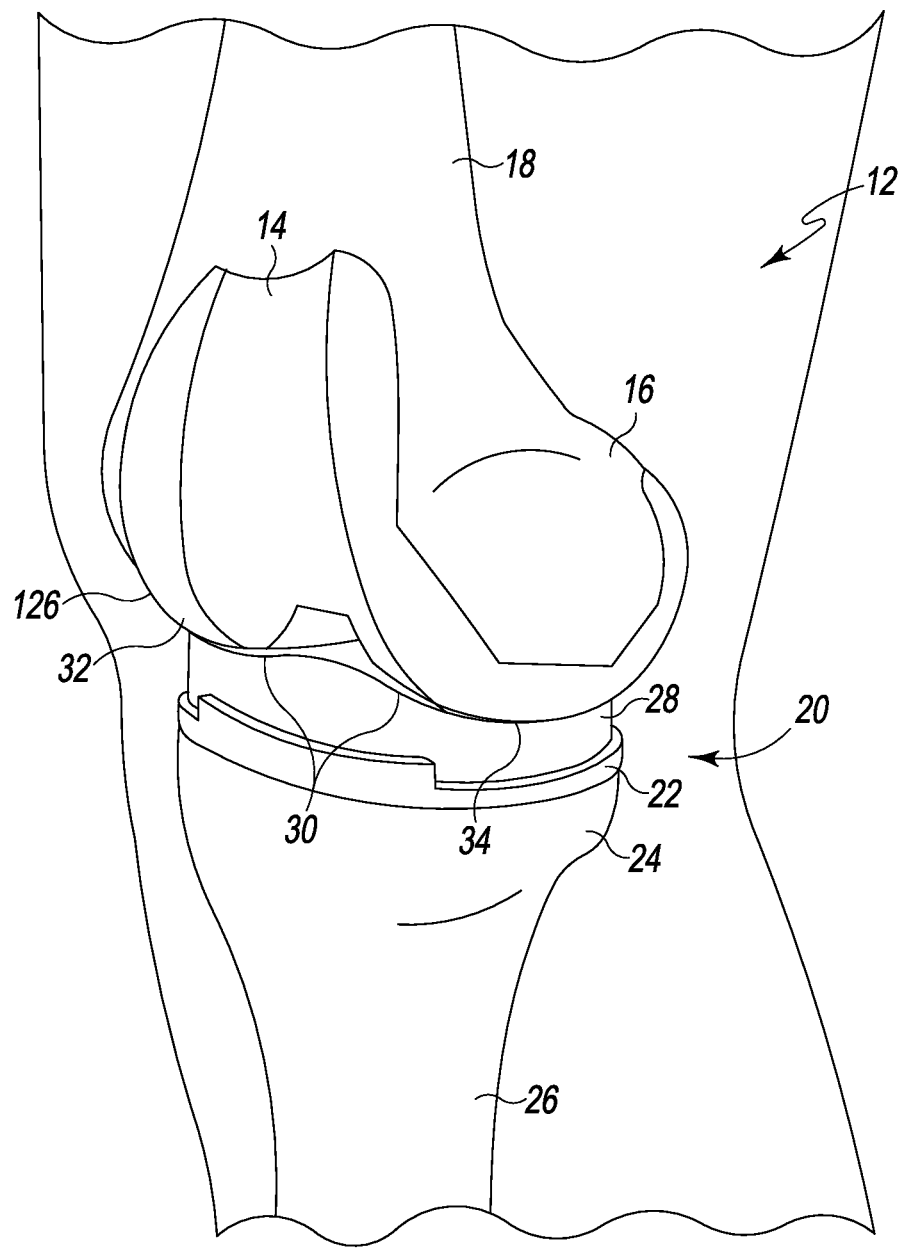
FIG. 2 is a perspective view of a primary orthopaedic knee prosthesis implanted in a patient's body.

In some embodiments, one or more customized patient-specific orthopaedic surgical instruments may be customized to engage one or more prosthetic components of a primary knee prosthesis such as the primary knee prosthesis 12 shown in FIG. 2. The primary knee prosthesis 12 includes a primary femoral prosthetic component 14 secured to a distal end 16 of a patient's femur 18 and a primary tibial prosthetic component 20. In the illustrative embodiment, the primary tibial prosthetic component 20 includes a tibial tray 22 secured to a proximal end 24 of a patient's tibia 26 and a tibial bearing 28 that is positioned between the tibial tray 22 and the primary femoral prosthetic component 14. The tibial bearing 28 includes a pair of curved concave bearing surfaces 30 that engage a pair of corresponding curved convex condyle surfaces 32, 34 of the primary femoral prosthetic component 14. As described in greater detail below, a customized patient-specific orthopaedic surgical instrument may be configured to engage, for example, one or both of the condyle surfaces 32, 34 of the primary femoral prosthetic component 14 to position the customized patient-specific orthopaedic surgical instrument relative to the distal end 16 of the patient's femur 18. Another customized patient-specific orthopaedic surgical instrument may be configured to engage part of the tibial tray 22 to position the patient-specific orthopaedic surgical instrument relative to the proximal end 24 of the patient's tibia 26. In some embodiments, the customized patient-specific instrument may be configured to engage the tibial tray 22 and the femoral prosthetic component 14.

Figure 3:
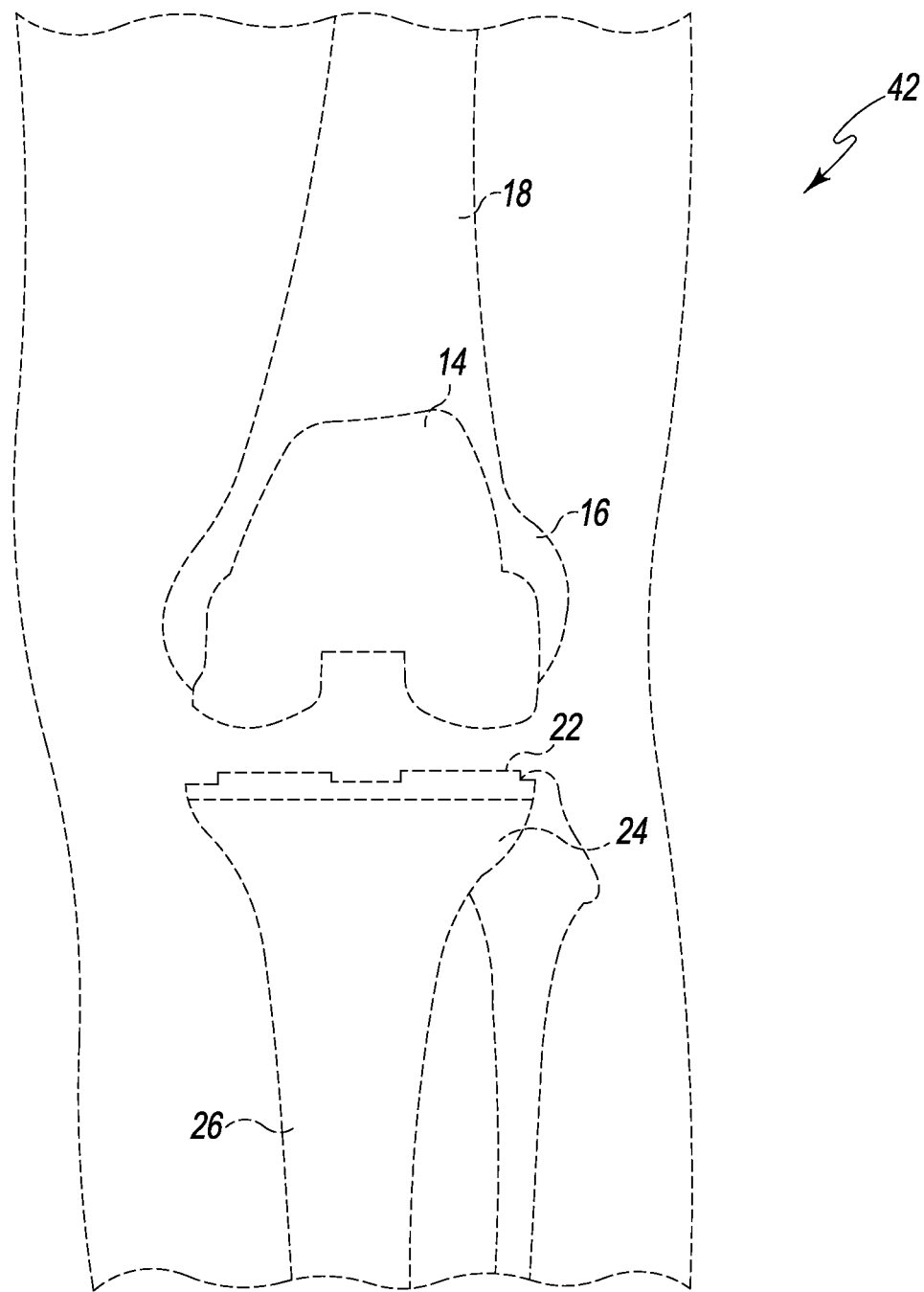
FIG. 3 is a converted image of the primary orthopaedic knee prosthesis of FIG. 2.

Returning to FIG. 1, the algorithm 10 includes process steps 38 and 40, in which an orthopaedic surgeon performs pre-operative planning of the orthopaedic surgical procedure to be performed on a patient. The process steps 38 and 40 may be performed in any order or contemporaneously with each other. In process step 38, a number of medical images of the relevant area of the patient are generated, including images of the bony anatomy or joint and the previously-implanted primary prosthesis. Those images may include, for example, an image 42 of the anterior portion of the patient's bones, which, as shown in FIG. 3, illustrates the position the primary femoral prosthetic component 14 on the distal end 16 of the patient's femur 18 and the tibial tray 22 on the proximal end 24 of the patient's tibia 26.

To do so, the orthopaedic surgeon or other healthcare provider may operate an imaging system to generate the medical images. The medical images may be embodied as any number and type of medical images capable of being used to generate a three-dimensional rendered model of the patient's previously-implanted prosthesis and bony anatomy or relevant joint. For example, the medical images may be embodied as any number of computed tomography (CT) images, magnetic resonance imaging (MRI) images, or other three-dimensional medical images. Additionally or alternatively, as described in more detail below in regard to process step 44, the medical images may be embodied as a number of X-ray images or other two-dimensional images from which a three-dimensional rendered model of the patient's previously-implanted prosthesis and relevant bony anatomy may be generated.

In process step 40, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for the resection level of the patient's bone, femoral rotation of the revision prosthesis, revision prosthesis size preferences, tibial slope, and details of any observed patient abnormalities during primary postoperative care and monitoring. In some embodiments, the orthopaedic surgeon's preferences are saved as a surgeon's profile, which may used as default constraint values for further surgical plans.

In some embodiments, the medical images and the constraint data, if any, may be transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor may process the images in process step 44. In other embodiments, the images may be processed locally.

In process step 44, the medical images are processed to facilitate the determination of the bone cutting planes, implant sizing, and fabrication of the customized patient-specific orthopaedic surgical instrument as described in more detail below. For example, in process step 46, the medical images may be converted to generate three-dimensional images. For example, in embodiments wherein the medical images are embodied as a number of two-dimensional images, a suitable computer algorithm may be used to generate one or more three-dimensional images from the number of two-dimensional images. Additionally, in some embodiments, the medical images may be generated based on an established standard such as the Digital Imaging and Communications in Medicine (DICOM) standard. In such embodiments, an edge-detection, thresholding, watershead, or shape-matching algorithm may be used to convert or reconstruct images to a format acceptable in a computer aided design application or other image processing application. Further, in some embodiments, an algorithm may be used to account for tissue such as ligaments not discernable in the generated medical images. In such embodiments, any three-dimensional model of the patient-specific instrument (see, e.g., process step 76 below) may be modified according to such algorithm to increase the fit and function of the instrument.

In process step 48, the medical images and/or the converted/reconstructed images from process step 46 may be processed to determine a number of landmarks of the patient's bony anatomy and the implanted knee prosthesis. To do so, the vendor may use any suitable algorithm to process the images. Depending on the surgical procedure, the landmarks the bony anatomy may include, for example, the patient's femoral epicondyles, femoral intramedullary canal, tibial intramedullary canal, fibula head, tibia tubercle, hip center, ankle center, and/or other aspects of the patient's bony anatomy. In a revision surgery for one of the patient's knees, the joint line of the patient's other knee may also be identified. What is meant herein by "joint line" in reference to the patient's bony anatomy is the line of contact between the distal end of the patient's femur and the proximal end of the patient's tibia.

Additionally, a number of landmarks of the implanted primary prosthesis may be determined from the medical images and/or the converted/reconstructed images. Those landmarks may include, for example, the most distal medial point, the most distal lateral point, most posterior medial point, and most posterior lateral point of the primary femoral prosthetic component. The tibial plateau points may also be determined along with the most proximal medial point, most proximal lateral point, most posterior medial point, and most posterior lateral point of the primary tibial prosthetic component such as, for example, the implanted tibial tray.

Figure 4:
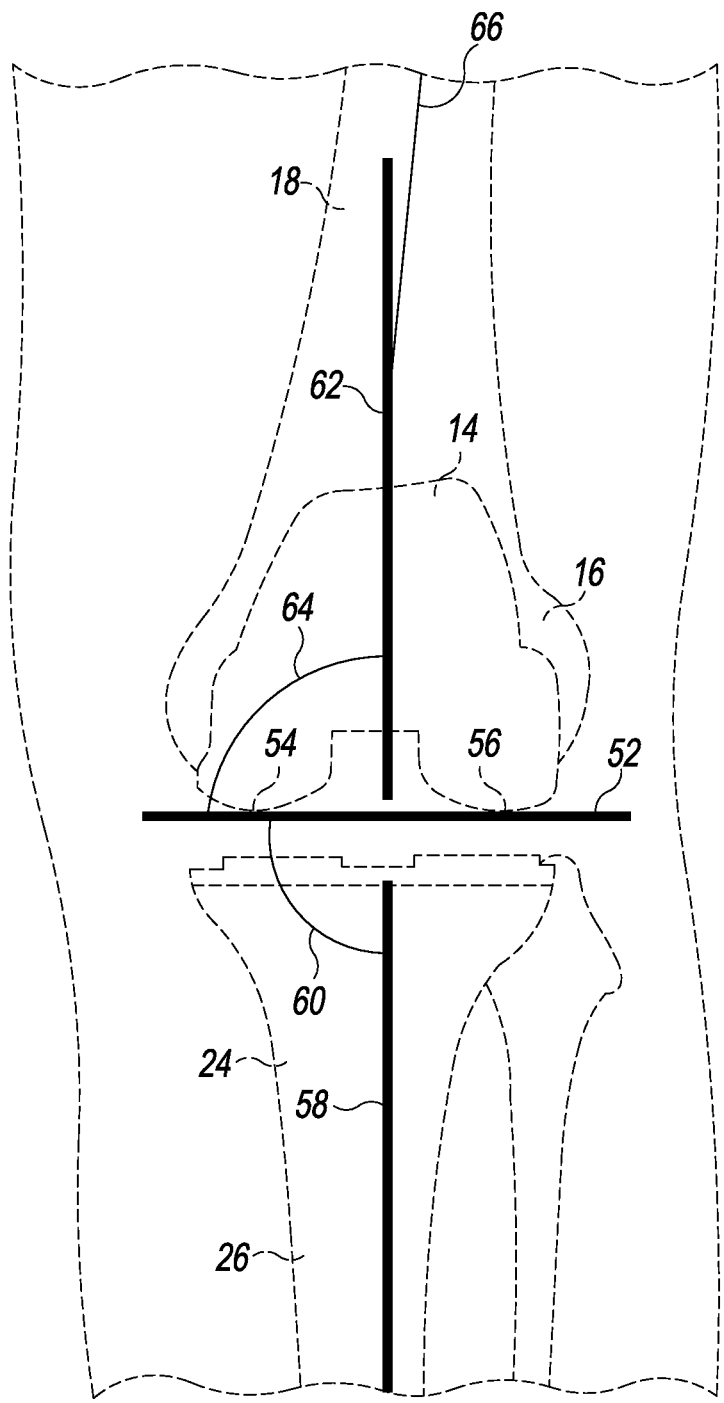
FIG. 4 is a view similar to FIG. 3 showing a pre-operative assessment of the primary orthopaedic knee prosthesis.

In the process step 50, the landmarks identified in process step 48 may be used to determine the alignment of patient's bones and the implanted primary prosthesis. For example, as shown in FIG. 4, a joint line 52 of the implanted primary prosthesis may be determined by locating the most distal medial point and the most distal lateral point of the primary femoral prosthetic component when the patient's leg is in extension. In reference to knee prosthetic components, the term "joint line" refers to the contact line between the prosthetic femoral component and the prosthetic tibial bearing of the knee prosthesis. As shown in FIG. 4, the joint line 52 is established by the most distal medial point 54 and the most distal lateral point 56 of the femoral prosthetic component 14.

Other landmarks may be used to establish other aspects of the present alignment of the patient's bone. For example, the ankle center may be used to locate and define the center of the patient's talus, and the center of the patient's talus may be used with the orientation of the primary tibial tray 22 to establish the tibial mechanical axis 58. The varus angle 60 of the patient's tibia 26 may then be determined.

Figure 5:
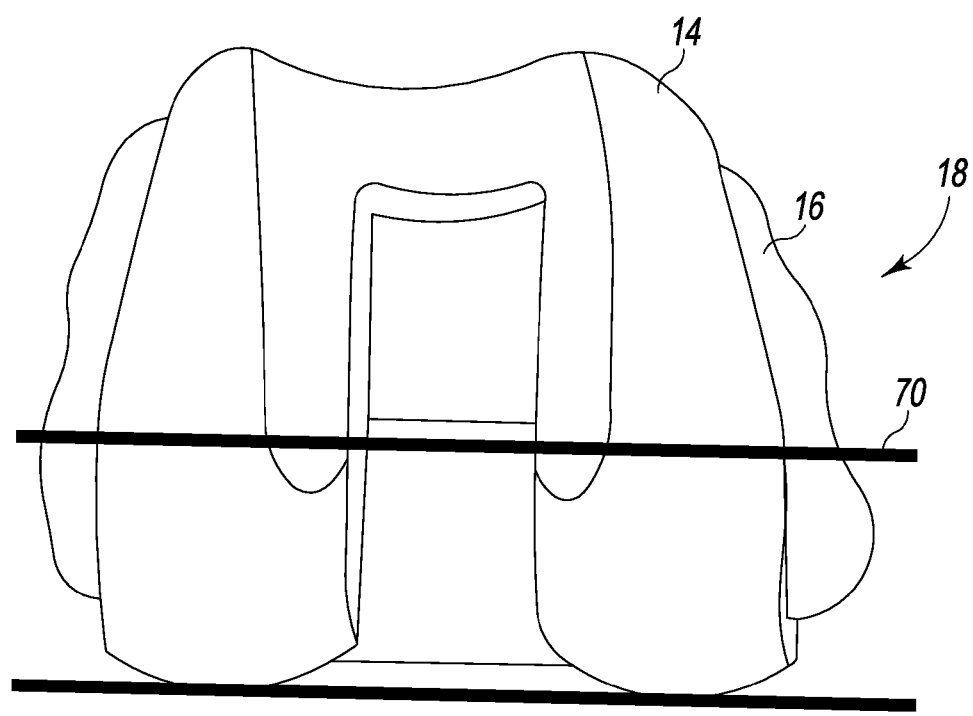
FIG. 5 is another view of the primary orthopaedic knee prosthesis of FIG. 2 and the pre-operative assessment.

Similarly, the hip center may be used to establish the patient's femoral head, which may be subsequently used with the orientation of the primary femoral prosthetic component 14 to establish the femoral mechanical axis 62. As shown in FIG. 4, the valgus angle 64 may then be determined. Additionally, the location of the femoral anatomical axis 66 may be calculated by locating the center of the distal shaft (not shown) of the primary femoral prosthetic component 14. As shown in FIG. 5, the femoral medial and lateral epicondyles may be used to create the epicondylar axis 70, which may be used to establish the femoral rotation of the primary femoral prosthetic component 14.

Figure 6:
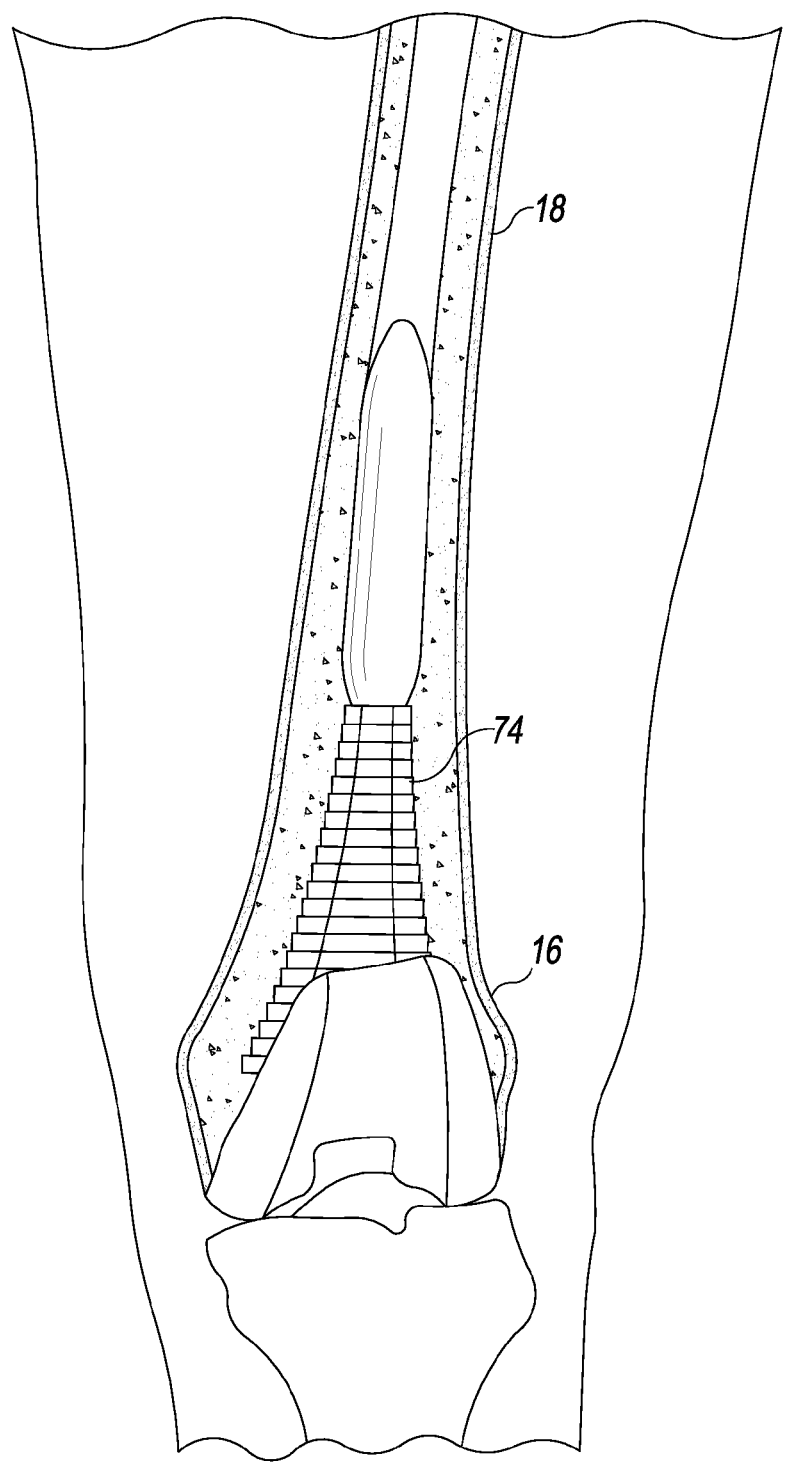
FIG. 6 is an anterior view of a three-dimensional model of the patient's body including a digital template of a revision orthopaedic knee prosthesis.
Figure 7:
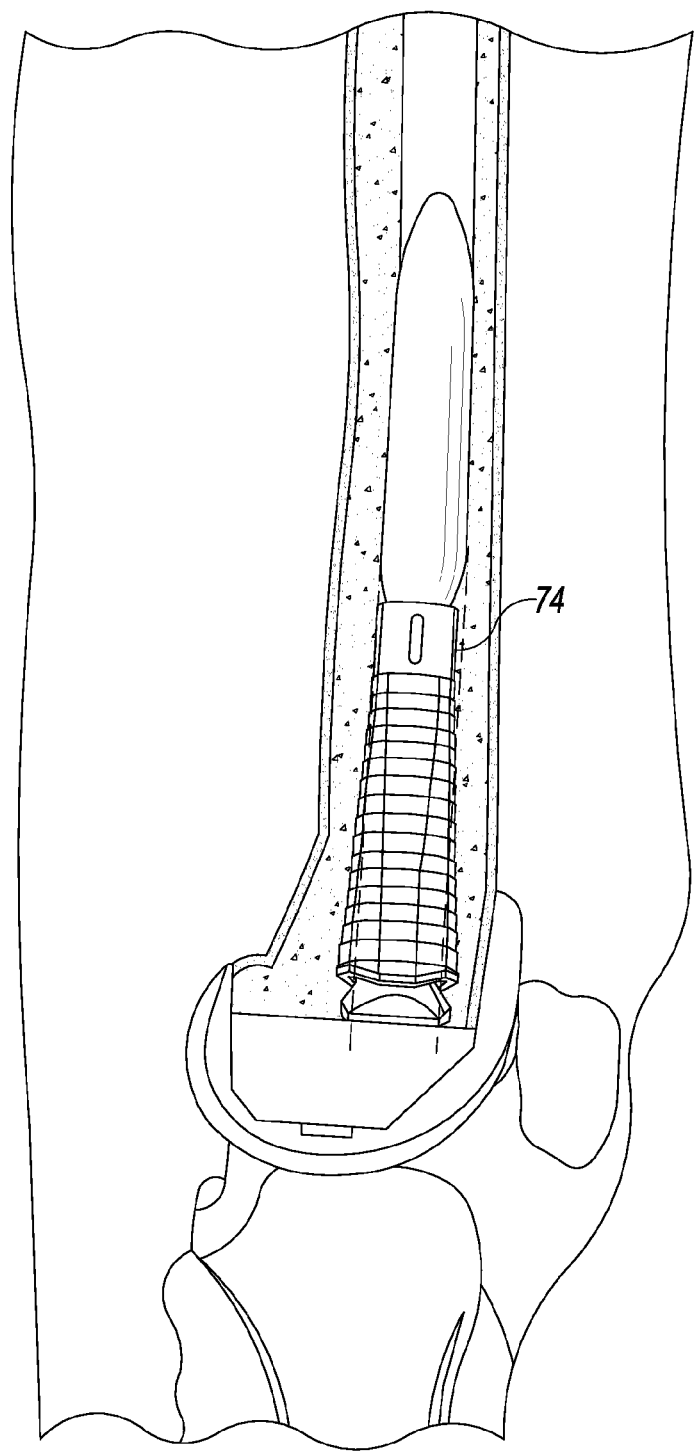
FIG. 7 is a medial view of the three-dimensional model of the patient's body including the digital template of the revision orthopaedic knee prosthesis.

In process step 50, a digital template 74 of the primary orthopaedic prosthesis may be overlaid onto one or more of the processed medical images, as shown in, for example, FIGS. 6 and 7. The vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Any one or more other aspects of the patient's bony anatomy may also be used to determine the proper positioning of the digital template. Additionally, the landmarks of the primary orthopaedic prosthesis identified in process step 48 may be used to determine the proper positioning of the digital template.

In process step 72, a surgical plan is generated. As part of the surgical plan, the cutting planes of the patient's bone may be determined. The planned cutting planes are determined based on the type, size, and position of the orthopaedic prosthesis to be used during the orthopaedic surgical procedure, on the processed images such as specific landmarks identified in the images, and on the constraint data supplied in process steps 38 and 40. The type and/or size of the orthopaedic prosthesis may be determined based on the patient's anatomy and the constraint data. For example, the constraint data may dictate the type, make, model, size, or other characteristic of the orthopaedic prosthesis.

The selection of the revision orthopaedic prosthesis may also be modified based on the medical images. For example, as shown in FIGS. 6 and 7, a digital template 74 of the revision orthopaedic prosthesis may be overlaid onto one or more of the processed medical images. The digital template 74 may be a three-dimensional model of the revision orthopaedic prosthesis, which accurately reproduces the dimensions of the actual prosthesis. The model may be included in a library of such three-dimensional models. The vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template. As such, the surgeon and/or vendor may select a revision orthopaedic prosthesis that is usable with the bony anatomy of the patient and that matches the constraint data or preferences of the orthopaedic surgeon.

The digital template along with surgical alignment parameters may be used to generate the surgical plan document. The document may include the revision implant's target rotation with respect to bony landmarks such as the femoral epicondyle, posterior condyles, and the mechanical axis as defined by the hip, knee, and/or ankle centers. The document may also include the planned target joint line for the revision orthopaedic prosthesis, the target valgus angle, and the target varus angle.

The planned cutting planes for the patient's bone(s) may then be determined based on the determined size, location, and orientation of the orthopaedic prosthesis. In addition, other aspects of the patient's bony anatomy, as determined in process step 44, may be used to determine or adjust the planned cutting planes. For example, the determined mechanical axis, landmarks, and/or other determined aspects of the relevant bones of the patient may be used to determine the planned cutting planes.

In process step 76, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The particular type of orthopaedic surgical instrument to be modeled and fabricated may be determined based on the orthopaedic surgical procedure to be performed, the constraint data, and/or the type of orthopaedic prosthesis to be implanted in the patient. As such, the customized patient-specific orthopaedic surgical instrument may be embodied as any type of orthopaedic surgical instrument for use in the performance of an orthopaedic surgical procedure. For example, the orthopaedic surgical instrument may be embodied as a bone-cutting block, a drilling/pinning guide, a milling guide, and/or any other type of orthopaedic surgical tool or instrument.

The particular shape of the customized patient-specific orthopaedic surgical instrument is determined based on the planned location of the orthopaedic surgical instrument relative to the patient's bony anatomy and, in some embodiments, the implanted primary prosthesis. The location of the customized patient-specific orthopaedic surgical instrument is determined based on the type and determined location of the orthopaedic prosthesis to be used during the orthopaedic surgical procedure. That is, the planned location of the customized patient-specific orthopaedic surgical instrument relative to the patient's bony anatomy may be selected based on, in part, the planned cutting planes of the patient's bone(s) as determined in step 72.

For example, in embodiments in which the customized patient-specific orthopaedic surgical instrument is embodied as a drilling/pinning guide (or hereinafter, simply a "pin guide") for use in conjunction with a patient-universal cutting block, the location of the orthopaedic surgical instrument is selected to position guide pins in the bone for use with the patient-universal cutting block. The guide pins, when used with one or more customized alignment guides, may align the cutting guide of the patient-universal cutting block with one or more of the planned cutting planes determined in process step 72. Additionally, the planned location of the orthopaedic surgical instrument may be based on the identified landmarks of the patient's bone identified in process steps 48 and 50.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-contacting surface having a negative contour that matches the contour of a portion of the bony anatomy of the patient such that the orthopaedic surgical instrument may be coupled to the bony anatomy of the patient in a unique location, which corresponds to the pre-planned location for the instrument. As described above, the customized patient-specific orthopaedic surgical instrument may also include a prosthesis-engaging surface having a negative contour that matches the contour of a portion of the implanted primary prosthesis of the patient. The customized patient-specific orthopaedic surgical instrument may be configured to interface with a patient-universal instrument to position the patient-universal instrument in a preplanned location relative to the bone or bones of the patient. When the customized patient-specific orthopaedic surgical instrument is coupled to the patient's bony anatomy, the implanted primary prosthesis, and/or patient-universal instrument in the unique location, one or more guides (e.g., cutting or drilling guide) may be aligned with one or more of the bone cutting plane(s) as described above.

Referring back to FIG. 1, after the model of the customized patient-specific orthopaedic surgical instrument has been generated in process step 76, the model is validated in process step 78. The model may be validated by, for example, analyzing the rendered model while coupled to the three-dimensional model of the patient's anatomy to verify the correlation of cutting guides and planes, drilling guides and planned drill points, and/or the like. Additionally, the model may be validated by transmitting or otherwise providing the model generated in step 78 to the orthopaedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopaedic surgeon for validation.

After the model has been validated in process step 78, the customized patient-specific orthopaedic surgical instrument is fabricated in process step 80. The customized patient-specific orthopaedic surgical instrument may be fabricated using any suitable fabrication device and method. Additionally, the customized patient-specific orthopaedic instrument may be formed from any suitable material such as a metallic material, a plastic material, or combination thereof depending on, for example, the intended use of the instrument. The fabricated customized patient-specific orthopaedic instrument is subsequently shipped or otherwise provided to the orthopaedic surgeon. The surgeon performs the orthopaedic surgical procedure in process step 82 using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

Figure 8:
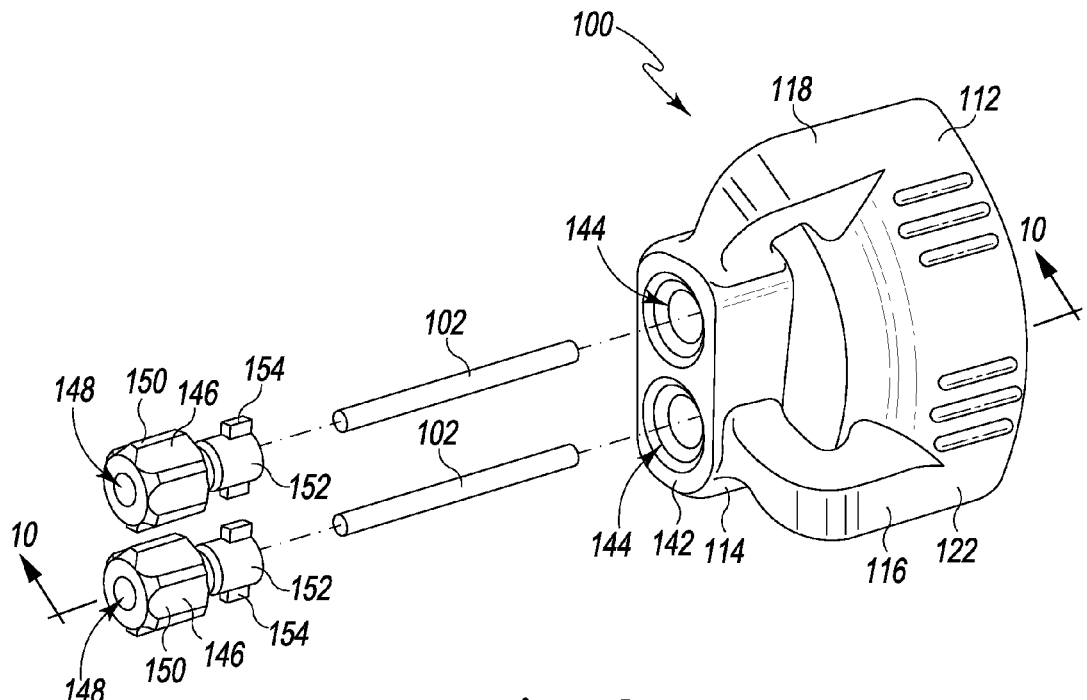
FIG. 8 is an exploded perspective view of a customized patient-specific femoral pin guide and a pair of removable drill bushings.
Figure 9:
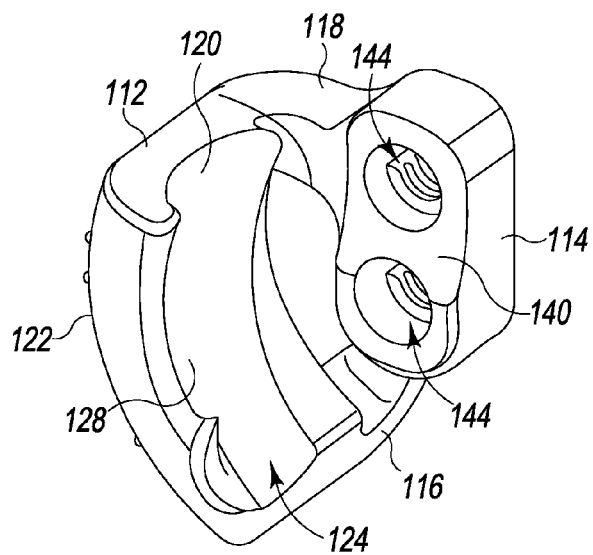
FIG. 9 is a perspective view of the customized patient-specific femoral pin guide of FIG. 8 showing a negative contour.
Figure 10:
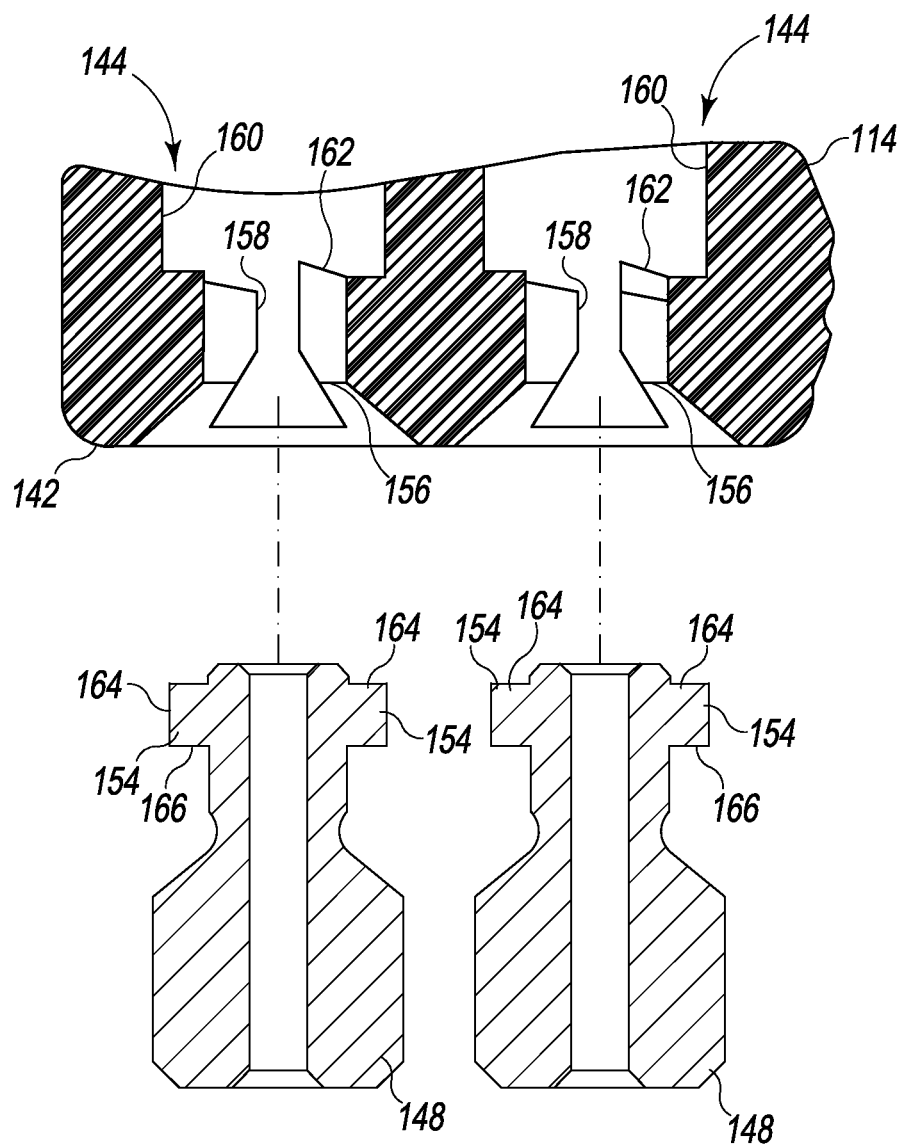
FIG. 10 is a cross section view of the customized patient-specific femoral pin guide and the removable drill bushings taken along the line 10-10 of FIG. 8, as viewed in the direction of the arrows.

Referring now to FIGS. 8-10, a customized patient-specific orthopaedic surgical instrument is shown as a femoral pin guide 100. In the illustrative embodiment, the pin guide 100 is configured to be coupled to the distal end 16 of the patient's femur 18 and the primary femoral prosthetic component 14 of the primary knee prosthesis 12. As described in greater detail below, the femoral pin guide 100 is used to install a pair of guide pins 102 in a location on the femur 18 that has been preplanned and customized for that particular patient. In the illustrative embodiment, the pin guide 100 is configured such that the guide pins 102 are inserted into the medial side of the distal end 16 of the patient's femur 18. It should be appreciated that in other embodiments the pin guide 100 may be configured to insert the pins 102 into the lateral side or anterior side of the patient's femur 18.

In the illustrative embodiment, the femoral pin guide 100 is devoid of a cutting guide; as such, other cutting blocks are required to resect and shape the distal end 16 of the patient's femur 18 to receive a revision femoral prosthetic component. Those other cutting blocks may be patient-universal cutting blocks such as, for example, a distal cutting block 104 (see FIG. 11) and a 4-in-1 cutting block 106 (see FIG. 14). As described in greater detail below, other customized patient-specific orthopaedic surgical instrument, such as an alignment bracket 108 (see FIGS. 11-13) and alignment guide 110

(see FIGS. 14-15), may be fabricated to engage the custom-located guide pins 102 and position the universal cutting blocks in preplanned positions and orientations. Such an arrangement permits a certain degree of customization of the surgical procedure by customizing the placement of the guide pins 102 to the patient's anatomy, while also enjoying the cost benefits associated with the use of reusable patient-universal cutting blocks. It should also be appreciated that in other embodiments the guide pins 102 may be located such that the patient-universal guide blocks may be installed directly on the guide pins 102. In yet other embodiments, the each cutting guide block may be a customized patient-specific cutting guide block configured to be installed on the guide pins 102.

As shown in FIG. 8, the pin guide 100 includes a main body 112 configured to engage the primary femoral prosthetic component 14 of the primary knee prosthesis 12 and a support body 114 configured to be coupled to the medial side of the distal end 16 of the patient's femur 18. The pin guide 100 also includes arms 116, 118, which connect the bodies 112, 114. The pin guide 100 may be formed from a material such as a plastic or resin material. In some embodiments, the pin guide 100 may be formed from a photo-curable or laser-curable resin. In one particular embodiment, the pin guide 100 is formed from a Vero resin using a rapid prototype fabrication process. It should be appreciated that in other embodiments the pin guide 100 may be formed from other materials in other embodiments. For example, in another particular embodiment, the pin guide 100 is formed from a polyimide thermoplastic resin, such as an Ultem resin. In the illustrative embodiment described herein, the pin guide 100 is embodied as a monolithic structure.

The main body 112 of the pin guide 100 includes a prosthesis-engaging surface 120 and an outer surface 122 opposite the prosthesis-engaging surface 120. The outer surface 122 is contoured to be gripped by the surgeon or other user. As shown in FIG. 9, the prosthesis-engaging surface 120 of the main body 112 includes a negative contour 124 that is configured to receive a portion of a medial condyle 126 (see FIG. 2) of the primary femoral component 14 having a corresponding contour. In the illustrative embodiment, the negative contour 124 of pin guide 100 includes a curved inner surface 128 that is shaped to match the curved condyle surface 32 of the medial condyle 126. The customized patient-specific negative contour 124 of the prosthesis-engaging surface 120 permits the pin guide 100 to be positioned on the patient's primary femoral component 14 (and hence the patient's femur 18) in a unique pre-determined location and orientation, as described in greater detail below.

It should be appreciated that in other embodiments the customized patient-specific pin guide may be configured to engage other portions of the primary femoral prosthetic component. For example, the pin guide might include a negative contour that is configured to receive a portion of a lateral condyle of the primary femoral component and/or a negative contour that is configured to receive a portion of the trochlear geometry of the primary femoral component. In other embodiments, the pin guide might include a negative contour that is configured to receive a portion of the anterior flange of the primary femoral component.

The support body 114 of the pin guide 100 includes a bone-contacting or bone-facing surface 140 and an outer surface 142 opposite the bone-facing surface 140. As shown in FIG. 8, the bone-facing surface 140 is a lateral surface configured to face the medial side of the distal end 16 of the patient's femur 18. The support body 114 has a number of guide holes 144 extending therethrough. A removable drill bushing 146 is locked into each guide hole 144. As will be described below in greater detail, the removable drill bushings 146 may be installed in the pin guide 100 for use in a surgical procedure and then removed from the pin guide 100. Whereas the pin guide 100 is customized and may be disposed after a single use on the patient for which it was made, the removed drill bushings 146 may be sterilized and reused in a subsequent surgical procedure.

As shown in FIG. 9, the bone-facing surface 140 of the support body 114 is substantially smooth. It should be appreciated that in other embodiments the bone-facing surface 140 may include a negative contour configured to receive a portion of the distal end 16 of the patient's femur 18 having a corresponding contour. In such embodiments, the negative contour of the bone-facing surface 140, in conjunction with the negative contour 124 of the prosthesis-engaging surface 120, permits the positioning of the pin guide 100 on the patient's femur 18 in a unique predetermined location and orientation.

As described above, a pair of removable drill bushings 146 may be attached to the pin guide 100. As shown in FIG. 8, each removable drill bushing 146 includes an elongated bore 148 that extends therethrough. The bore 148 is sized to receive a drill such that the patient's femur may be pre-drilled prior to installation of the guide pins 102. In the illustrative embodiment, each end of the bore 148 is countersunk. Each removable drill bushing 146 also includes a head 150 that is contoured to be gripped by a surgeon's fingers. The countersunk opening on the drill bushing's head 150 functions as a lead-in to facilitation insertion of the drill and the guide pins 102 into the bore 148.

A post 152 of the removable drill bushing 146 extends away from the head 150 and includes a locking flange 154 formed on the outer surface thereof. The locking flange 154 is utilized to lock the post 152 within one of the guide holes 144 of the pin guide 100. Specifically, as shown in FIG. 10, a locking slot 156 is formed in the support body 114 proximate to each of the guide holes 144. In the illustrative embodiment, the removable drill bushings 146 and locking slots 156 utilize a cam lock arrangement to secure the bushings 146 to the support body 114.

As shown in FIG. 9, the locking slot 156 includes two elongated channels 158 positioned on opposite sides of the guide hole 144 and an annular recess 160 formed within the support body 114. The outer ends of the channels 158 open to the outer surface 142 of the support body 114, with the inner ends of the channels 158 opening into the annular recess 160. A shoulder 162 defines the lateral side of the locking slot's annular recess 160. In the illustrative embodiment, the shoulder 162 is embodied as an angled cam surface. As will be described below, the locking flange 154 of the removable drill bushing 146 engages the cam surface to lock the removable drill bushing 146 to the pin guide 100.

The locking flange 154 is embodied as a pair of tabs 164 extending outwardly from opposite sides of its post 152. The tabs 164 are sized and positioned to be received into the respective channels 158 of the pin guide's locking slot 156. Specifically, to lock the removable drill bushing 146 to the pin guide 100, each of the tabs 164 is first aligned with one of the channels 158 and thereafter advanced into the channels 158. When the tabs 164 have been advanced into the channels 158 far enough to clear the shoulder 162, the head 150 of the removable drill bushing 146 may be rotated approximately 90 degrees, thereby also rotating the tabs 164. Such rotation of the tabs 164 removes the tabs from alignment with the channels 158 such that the tabs 164 are captured within the annular recess 160. Such rotation also causes the cam surface 166 of the tabs 164 to engage the cam surface of the shoulder 162 to lock the removable drill bushing 146 to the pin guide 100.

To unlock the removable drill bushing 146 from the pin guide 100, the head 150 of the removable drill bushing 146 may be rotated in the opposite direction it was rotated during installation to a position in which the tabs 164 are aligned with the channels 158. Once the tabs 164 are aligned in such a manner, the post 152 of the removable drill bushing 146 may be removed from the guide hole 144, thereby disassembling the removable drill bushing 146 from the pin guide 100.

It should be appreciated that in other embodiments the removable drill bushings 146 and locking slots 156 may utilize other locking arrangements to secure the bushings 146 to the support body 114. For example, the bushings 146 may include external threads that threadingly engage the locking slots 156.

Figure 11:
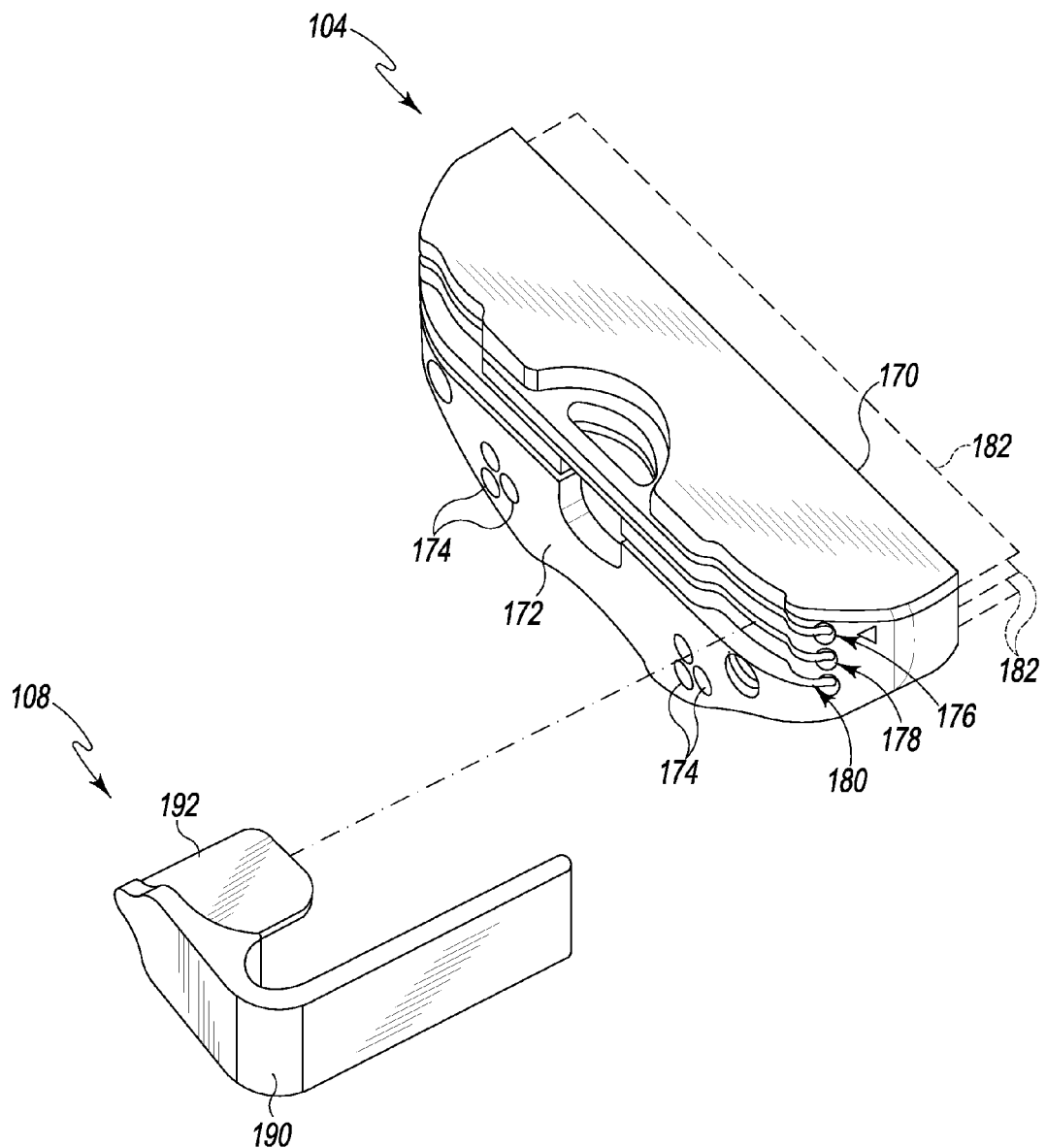
FIG. 11 is a perspective view of a customized patient-specific alignment bracket and a distal cutting guide block.

Referring now to FIGS. 11-14, a patient-universal distal cutting block 104 is shown with another customized patient-specific orthopaedic surgical instrument 108. In the illustrative embodiment, the customized patient-specific orthopaedic surgical instrument 108 is embodied as an alignment guide or bracket 108, which engages the custom-located guide pins 102 to position the distal cutting block 104 in a preplanned position and orientation. As shown in FIG. 11, the distal cutting block 104 includes a posterior side wall 170 that confronts the anterior surface of the femur 18 when the distal cutting block 104 positioned thereon. The distal cutting block 104 also includes an anterior side wall 172 positioned opposite the posterior side wall 170. A number of guide pin holes 174 extend through the side walls 170, 172. In the illustrative embodiment, the distal cutting block 104 includes four different pairs of guide pin holes 174.

The distal cutting block 104 includes a number of distal cutting guides 176, 178, 180 that may be used to guide the resection of the distal end 16 of the patient's femur 18. In the illustrative embodiment, each cutting guide 176 is embodied as a captured cutting guide (i.e., it is closed on all sides so as to capture a saw blade therein) and includes an elongated slot extending in the medial/lateral direction. As shown in FIG. 11, the distal cutting block 104 has three distal cutting guides 176, 178, 180 extending through the side walls 170, 172. Each distal cutting guide defines a resection plane 182, which extends through the distal end 16 of the patient's femur 18 when the distal cutting block 104 is positioned thereon. Each of the distal cutting guides 176, 178, 180 is sized and shaped to receive the blade (not shown) of a surgical saw or other cutting instrument and orient the blade to resect the distal surfaces of the patient's femur during an orthopaedic surgical procedure. In that way, the cutting guides 176, 178, 180 may be used by the orthopaedic surgeon during the resection of the patient's femur and, more specifically, during the resection of the distal surfaces of the patient's femur 18. Because the cutting guides 176, 178, 180 are used to resect the distal surfaces of the patient's femur, the amount of material removed by each cutting guide affects the position of the joint line of the revision orthopaedic prosthesis.

For example, the cutting guide 176 of the cutting block 104 is the baseline or "zero" setting. If the surgeon desires to elevate the joint line of the revision orthopaedic prosthesis (or use a prosthetic augment component), more bone may be removed from the distal end 16 of the femur 18 than would be removed by use of the zero setting. To do so, the surgeon may use the cutting guide 178, which is spaced apart from the cutting guide 176 by approximately four millimeters in the illustrative embodiment. The cutting guide 178 is thus the "+4 mm" setting in the illustrative embodiment. If the surgeon desires to remove still more bone (and hence further elevate the joint line), the surgeon may use the cutting guide 180, which is spaced apart from the cutting guide 176 by approximately four millimeters and is thus the "+8 mm" setting. In other embodiments, the distal cutting block 104 may include any number of cutting guides, which may be spaced apart by an amount greater than or less than four millimeters.

As described above, the customized patient-specific orthopaedic surgical instrument 108 (i.e., the alignment bracket 108) is configured to engage the distal cutting block 104 and the custom-located guide pins 102 to position the cutting block 104 in a preplanned location and orientation. In the illustrative embodiment, the alignment bracket 108 has an L-shaped body 190 that is configured to engage the guide pins 102 and a mounting flange 192 configured to be received in one of the cutting guides 176, 178, 180 of the distal cutting block 104. The alignment bracket 108 may be formed from a material such as a plastic or resin material. In some embodiments, the alignment bracket 108 may be formed from a photo-curable or laser-curable resin. In one particular embodiment, the alignment bracket 108 is formed from a Vero resin using a rapid prototype fabrication process. It should be appreciated that in other embodiments the alignment bracket 108 may be formed from other materials in other embodiments. For example, in another particular embodiment, the alignment bracket 108 is formed from a polyimide thermoplastic resin, such as an Ultem resin. In the illustrative embodiment described herein, the alignment bracket 108 is embodied as a monolithic structure.

Figure 12:
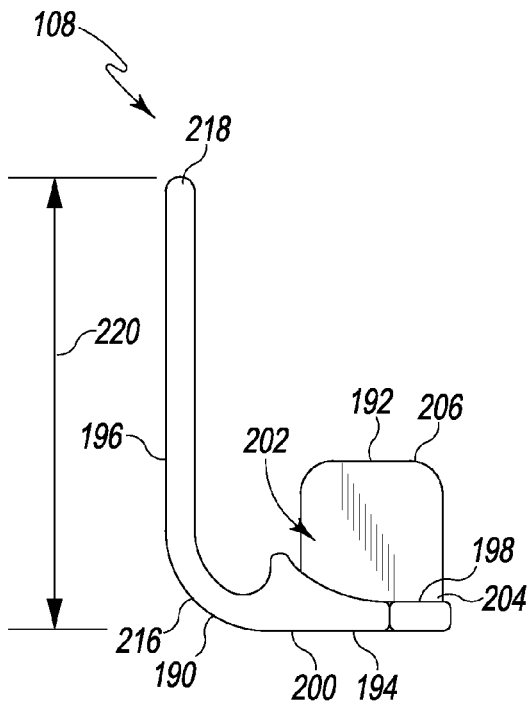
FIG. 12 is a plan view of the customized patient-specific alignment bracket of FIG. 11.

As shown in FIG. 12, the body 190 of the alignment bracket 108 includes an anterior arm 194 and a medial arm 196 extending away from the anterior arm 194. The anterior arm 194 has an inner surface 198 that faces the distal cutting block 104 and an outer surface 200 positioned opposite the inner surface 198. The inner surface 198 includes a negative contour 202 that is shaped to match a corresponding contour of the distal cutting block 104. In the illustrative embodiment, the contour 202 of the alignment bracket 108 is curved to match a curved section of the anterior side wall 172 of the distal cutting block 104.

Figure 13:
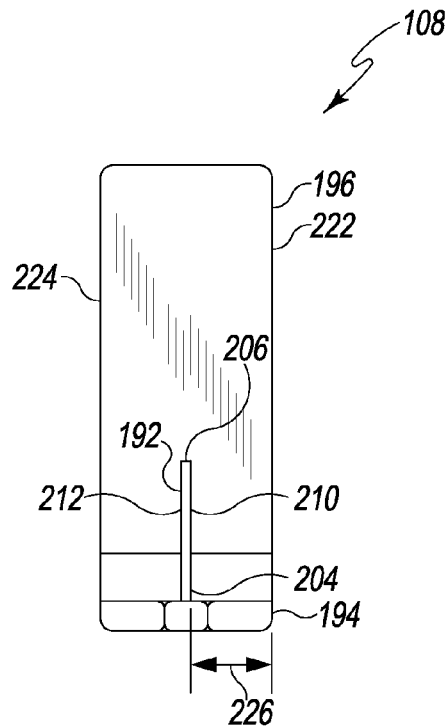
FIG. 13 is a side elevation view of the customized patient-specific alignment bracket of FIGS. 11-12.

The mounting flange 192 of the alignment bracket 108 has a base 204 that is attached to the inner surface 198 of the anterior arm 194 and a tip 206 that is spaced apart from the base 204. As shown in FIG. 13, the mounting flange 192 has a thickness 208 defined between a pair of substantially planar surfaces 210, 212. In the illustrative embodiment, the thickness 208 is slightly larger than each opening 214 of the cutting guides 176, 178, 180 of the distal cutting block 104. In that way, when the flange 192 of the alignment bracket 108 is inserted into one of the cutting guides 176, 178, 180, the surfaces 210, 212 engage the walls of that cutting guide to retain the flange 192 therein, thereby securing the alignment bracket 108 to the cutting block 104. In other embodiments, the mounting flange 192 and/or the body 190 may include a tab, lug, or other feature to secure the alignment bracket 108 to the cutting block 104.

As shown in FIGS. 12-13, the medial arm 196 of the alignment bracket 108 extends posteriorly from the anterior arm 194. The medial arm 196 is sized to engage the guide pins 102 when the alignment bracket 108 is secured to the cutting block 104 and the cutting block 104 is properly positioned relative to the patient's femur 18. As shown in FIG. 12, the medial arm 196 has an anterior end 216 attached to the anterior arm 194 and a posterior end 218. The medial arm 196 has a length 220 defined between the ends 216, 218, which is selected to permit the medial arm 196 to engage the pair of custom-located guide pins 102, which corresponds to the anterior-posterior width of the distal end 16 of the patient's femur 18.

As shown in FIG. 13, the medial arm 196 has a lower surface 222 configured to engage the guide pins 102 and an upper surface 224 positioned opposite the lower surface 222. In the illustrative embodiment, the surfaces 222, 224 are substantially planar. The alignment bracket 108 has a distance 226 defined between the lower surface 222 and the lower surface 210 of the mounting flange 192. The distance 226 is customized to a particular patient based on the planned location of the joint line of the revision orthopaedic prosthesis. The distance 226 is smaller when greater elevation of the joint line of the revision orthopaedic prosthesis is desired (i.e., when a larger distal cut of the distal end 16 of the femur is planned). For example, when it is desired to use the cutting guide 180 of the cutting block 104 (i.e., the "+8 mm" setting) to elevate the joint line, the distance 226 may be set to position the mounting flange 192 closer to the lower surface 222 such that the flange 192 may be received in the cutting guide 180.

In other embodiments, less elevation of the joint line of the revision orthopaedic prosthesis may be desired. In such embodiments, the distance 226 may be greater such that less material is removed from the distal end 16 of the femur 18. Thus, when it is desired to use the cutting guide 176 of the cutting block (i.e., the "zero" setting), the distance 226 may be set to position the mounting flange 192 farther from the lower surface 222. In that way, the flange 192 may be received in the cutting guide 176 to secure the alignment bracket 108 to the cutting block 104.

Figure 14:
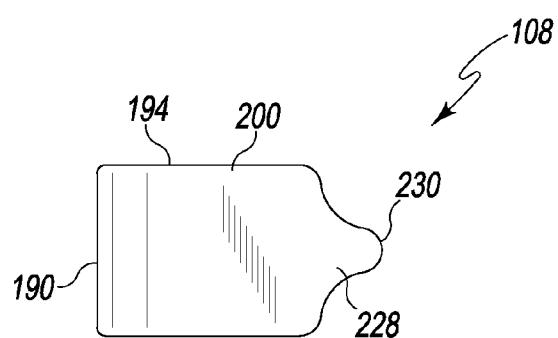
FIG. 14 is an anterior elevation view of the customized patient-specific alignment bracket of FIGS. 11-13.

As shown in FIG. 14, the alignment bracket 108 has an indicator 228 that shows the position of the mounting flange 192. In the illustrative embodiment, the indicator 228 is a tab or pointer 230 extending from the anterior arm 194. When the alignment bracket 108 is secured to the cutting block 104, the pointer 230 indicates the cutting guide slot in which the mounting flange 192 is received.

Figure 15:
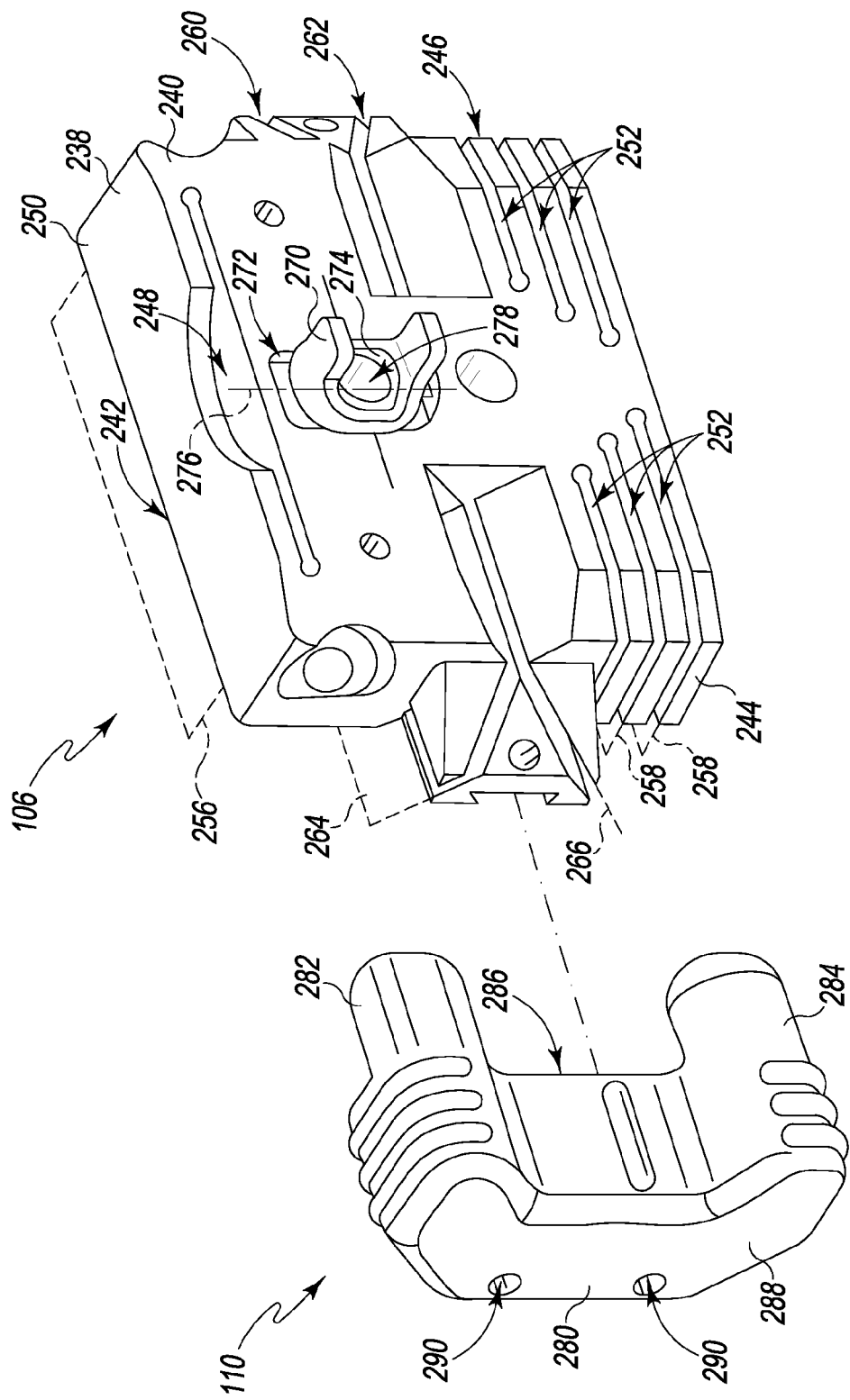
FIG. 15 is a perspective view of a customized patient-specific alignment guide and a 4-in-1 cutting guide block.
Figure 16:
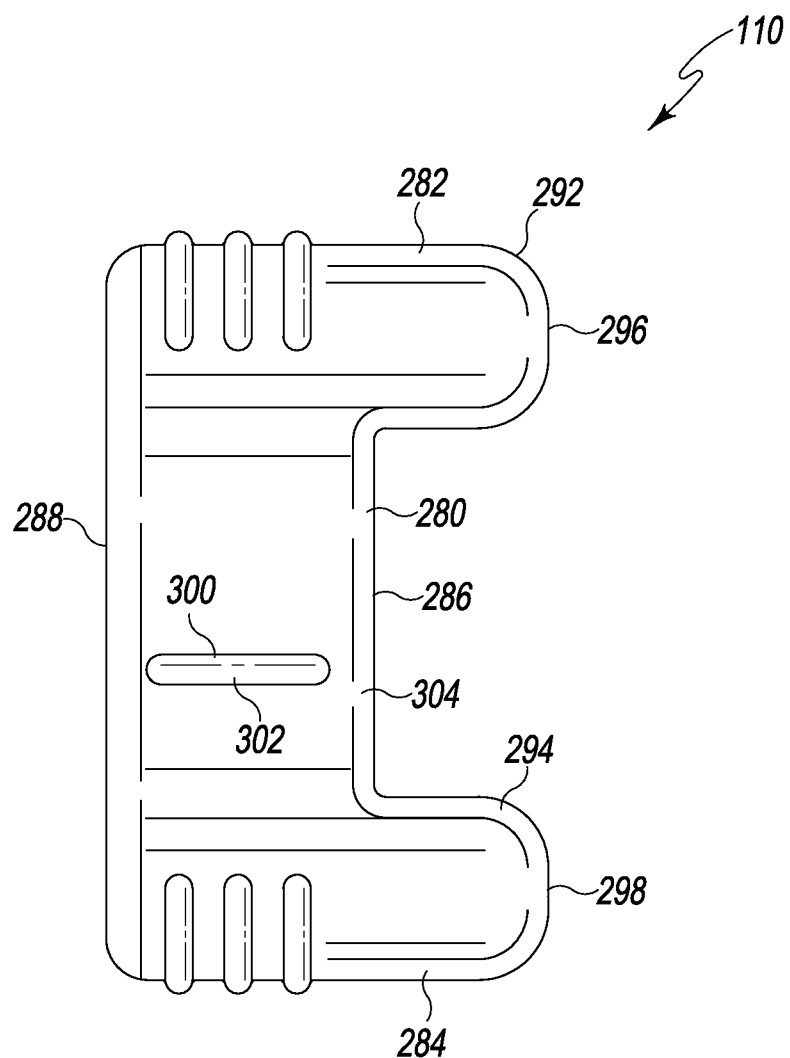
FIG. 16 is an anterior elevation view of the customized patient-specific alignment guide of FIG. 15.

Referring now to FIGS. 15-16, a patient-universal 4-in-1 cutting block 106 is shown with another customized patient-specific orthopaedic surgical instrument 110. In the illustrative embodiment, the customized patient-specific orthopaedic surgical instrument 110 is embodied as an alignment guide 110, which engages the custom-located guide pins 102 to position the 4-in-1 cutting block 106 in a preplanned position and orientation. As shown in FIG. 15, the 4-in-1 cutting block 106 includes a body 238 having an outer surface 240, a bone-engaging surface 242 positioned opposite the outer surface 240, a medial side wall 244 extending between the surfaces 240, 242, and a lateral side wall 246 positioned opposite the medial side wall 244. In the illustrative embodiment, the bone-engaging surface 242 of the 4-in-1 cutting block 106 confronts the distal surface of the femur 18.

The 4-in-1 cutting block 106 has an anterior cutting guide 248 formed near its anterior end 250 and a plurality of posterior cutting guides 252 formed near its posterior end 254. The anterior cutting guide 248 is an elongated slot extending in the medial/lateral direction and is embodied as a captured cutting guide (i.e., it is closed on all sides so as to capture a saw blade therein). The anterior cutting guide 248 extends through the entire thickness of the 4-in-1 cutting block 106— that is, the anterior cutting guide 248 extends through the cutting block's outer surface 240 and its bone-engaging surface 242. The cutting guide 248 defines a resection plane 256, which extends through the distal end 16 of the patient's femur 18 when the cutting block 106 is positioned thereon The anterior cutting guide 248 is sized and shaped to receive the blade (not shown) of a surgical saw or other cutting instrument and orient the blade to resect the anterior surface of the patient's femur during an orthopaedic surgical procedure.

Each posterior cutting guide 252 includes a pair of elongated slots extending in the medial/lateral direction. Each is embodied as a partially captured cutting guide (i.e., each is closed on three sides so as to capture a saw blade therein). Each posterior cutting guide 252 extends through the entire thickness of the 4-in-1 cutting block 106—that is, each posterior cutting guide 252 extends through the cutting block's outer surface 240 and its bone-engaging surface 242. Each cutting guide 252 defines a resection plane 258, which extends through the distal end 16 of the patient's femur 18 when the cutting block 106 is positioned thereon. Each cutting guide 252 is sized and shaped to receive the blade (not shown) of a surgical saw or other cutting instrument and orient the blade to resect the posterior surfaces of the patient's femur during an orthopaedic surgical procedure.

The 4-in-1 cutting block 106 has a pair of chamfer cutting guides 260, 262 formed near its middle. Specifically, the chamfer cutting guides 260, 262 are located posteriorly of the anterior cutting guide 248 and anteriorly of the posterior cutting guides 252. As shown in FIG. 15, the chamfer cutting guide 260 includes a pair of elongated slots extending in the medial/lateral direction. The chamfer cutting guide 260 is embodied as a partially captured cutting guide (i.e., it is closed on three sides so as to capture a saw blade therein). The chamfer cutting guide 260 extends through the entire thickness of the 4-in-1 cutting block 106—that is, the chamfer cutting guide 260 extends through the cutting block's outer surface 240 and its bone-engaging surface 242. The chamfer cutting guide 260 defines a resection plane 264, which extends through the distal end 16 of the patient's femur 18 when the cutting block 106 is positioned thereon. The chamfer cutting guide 260 is sized and shaped to receive the blade (not shown) of a surgical saw or other cutting instrument and orient the blade to perform an anterior chamfer cut of the patient's femur during an orthopaedic surgical procedure.

Similarly, the chamfer cutting guide 262 includes a pair of elongated slots extending in the medial/lateral direction. The chamfer cutting guide 262 is embodied as a partially captured cutting guide (i.e., it is closed on three sides so as to capture a saw blade therein). The chamfer cutting guide 262 extends through the entire thickness of the 4-in-1 cutting block 106— that is, the chamfer cutting guide 262 extends through the cutting block's outer surface 240 and its bone-engaging surface 242. The chamfer cutting guide 262 defines a resection plane 266, which extends through the distal end 16 of the patient's femur 18 when the cutting block 106 is positioned thereon. The chamfer cutting guide 262 is sized and shaped to receive the blade (not shown) of a surgical saw or other cutting instrument and orient the blade to perform a posterior chamfer cut of the patient's femur during an orthopaedic surgical procedure.

The 4-in-1 cutting block 106 also includes a bushing 270 that is moveable relative the body 238 of the 4-in-1 cutting block 106. As shown in FIG. 15, the bushing 270 is positioned in an elongated slot 272 extending in the anterior-posterior direction. The elongated slot 272 extends through the entire thickness of the 4-in-1 cutting block 106—that is, the elongated slot 272 extends through the cutting block's outer surface 240 and its bone-engaging surface 242. The bushing 270 has a cylindrical body 274 that is sized to be received in the slot 272 and may be moved along the longitudinal axis 276 of the slot 272 between the anterior and posterior ends of the slots 272. The bushing 270 also includes a bore 278 that extends through the cylindrical body 274. As described in greater detail below, the bore 278 is sized to receive an intramedullary shaft 310 (see FIG. 29). The 4-in-1 cutting block 106 also includes a locking mechanism (not shown) configured to lock the bushing 270 at any position along the axis 276 of the slot 272. It should be appreciated that in other embodiments the movable bushing 270 may be omitted and the bushing 270 may be integrally formed with the block 106 or otherwise fixed relative to it.

As described above, the customized patient-specific orthopaedic surgical instrument 110 (i.e., the alignment guide 110) is configured to engage the 4-in-1 cutting block 106 and the custom-located guide pins 102 to position the cutting block 106 in a preplanned location and orientation. In the illustrative embodiment, the alignment guide 110 includes a body 280 configured to engage the guide pins 102 and a pair of posts 282, 284 that extend laterally from the body 280. The alignment guide 110 may be formed from a material such as a plastic or resin material. In some embodiments, the alignment guide 110 may be formed from a photo-curable or laser-curable resin. In one particular embodiment, the alignment guide 110 is formed from a Vero resin using a rapid prototype fabrication process. It should be appreciated that in other embodiments the alignment guide 110 may be formed from other materials in other embodiments. For example, in another particular embodiment, the alignment guide 110 is formed from a polyimide thermoplastic resin, such as an Ultem resin. In the illustrative embodiment described herein, the alignment guide 110 is embodied as a monolithic structure.

The body 280 of the guide 110 includes a bone-facing surface 286 and an outer surface 288 positioned opposite the bone-facing surface 286. In the illustrative embodiment, the bone-facing surface is the lateral surface of the body 280 and the outer surface 288 is medial surface. The alignment guide 110 has a pair of guide pin holes 290 that extend through the entire thickness of the body 280—that is, each hole 290 extends through the cutting block's outer surface 288 and its bone-facing surface 286. The guide pin holes 290 are sized and positioned to receive the custom-located guide pins 102 such that the body 280 may be positioned on the guide pins 102 during the orthopaedic surgical procedure.

As shown in FIG. 16, the post 282 of the alignment guide 110 extends from the body 280 to a tip 292. Similarly, the other post 284 of the guide 110 extends from the body 280 to a tip 294. The tips 292, 294 have block-facing or block-engaging surfaces 296, 298, respectively, that are configured to engage the medial side wall 244 of the 4-in-1 cutting block 106. As described in greater detail below, the posts 282, 284 cooperate to define the femoral rotation of the cutting block 106 and hence the preplanned rotation of revision femoral component.

The alignment guide 110 also includes a marking 300 that indicates the preplanned anterior-posterior position of the 4-in-1 cutting block 106. As shown in FIG. 16, the marking 300 is embodied as an elongated tab 302 extending outwardly from the anterior surface 304 of the body 280. When the alignment guide 110 is positioned on the custom-located guide pins 102 and engages with the cutting block 106, the surgeon may align the anterior openings 306 of the chamfer cutting guides 260, 262 with the marking 300 to locate the cutting block 106 in the preplanned anterior-posterior position, as described in greater detail below.

Referring now to FIGS. 17-32, a surgeon may use the customized patient-specific femoral pin guide 100 to install a pair of guide pins 102 in locations on the femur 18 that have been customized for that particular patient. A customized patient-specific alignment bracket 108 may be secured to a patient-universal distal cutting block 104 and engaged with the custom-located pins 102 to locate the distal cutting block 104 in a unique preplanned orientation and position relative to the patient's femur 18. Thereafter, the distal cutting block 104 may be used to resect the distal surfaces of the patient's femur 18. A customized patient-specific alignment guide 110 may be secured to a patient-universal 4-in-1 cutting block 106 and installed on the custom-located pins 102 to locate the 4-in-1 cutting block 106 in a unique preplanned orientation and position relative to the patient's femur 18. Thereafter, the 4-in-1 cutting block 106 may be used to resect the anterior, posterior, and chamfer surfaces of the patient's femur 18. Such an arrangement permits a certain degree of customization of the surgical procedure by customizing the placement of the guide pins 102 to the patient's anatomy, while also enjoying the cost benefits associated with the use of reusable patient-universal cutting blocks.

Figure 17:
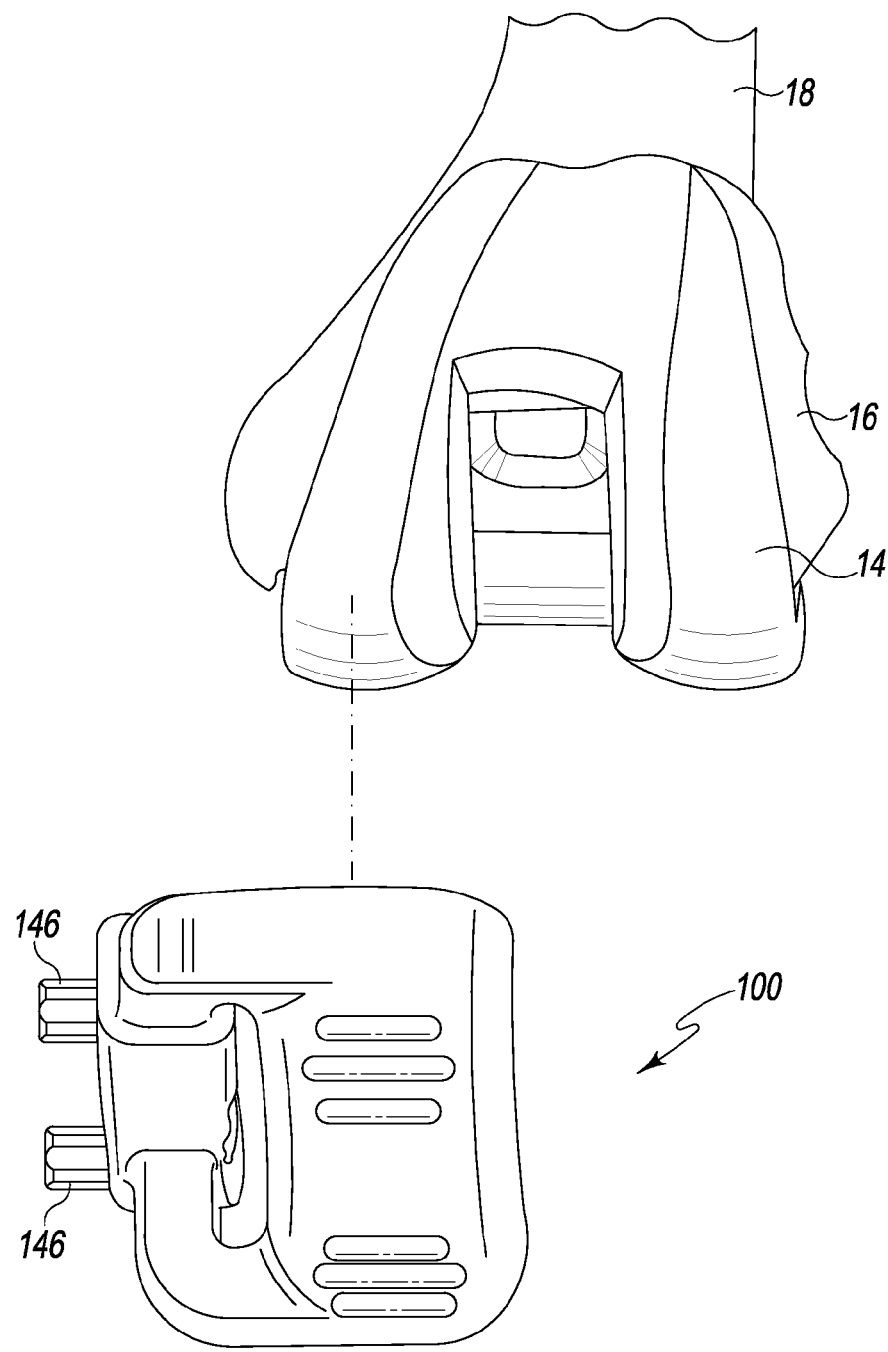
FIG. 17 is a perspective view of the primary femoral prosthetic component of FIG. 2 attached to a distal end of a patient's femur and the customized patient-specific femoral pin guide of FIG. 8.

As shown in FIG. 17, the surgical procedure commences with assembly of the customized patient-specific surgical instrument 100 on a prep table or other part of the surgery room. To do so, the surgeon first obtains a customized patient-specific pin guide 100 that was fabricated for the particular patient being treated by the surgeon. The pin guide 100, the alignment bracket 108, and the alignment guide 110 are fabricated in the manner described above in regard to FIGS. 1-7. Once the customized patient-specific pin guide 100 has been obtained, the surgeon then takes a pair of the sterilized removable drill bushings 146 and installs them in the pin guide 100. In particular, the surgeon may obtain a pair of the removable drill bushings 146 from a previous procedure (after being sterilized) or new drill bushings 146 (from the manufacturer's sterilized packaging). Thereafter, the surgeon inserts the post 152 of one of the drill bushings 146 into one of the guide holes 144 formed in the pin guide 100 and rotates the head 150 of the drill bushing 146 so that the tabs 164 are captured within the annular recess 160, as described above. The surgeon then obtains the other drill bushing 146 and installs it in the pin guide's other guide hole 144 in a similar manner.

Figure 18:
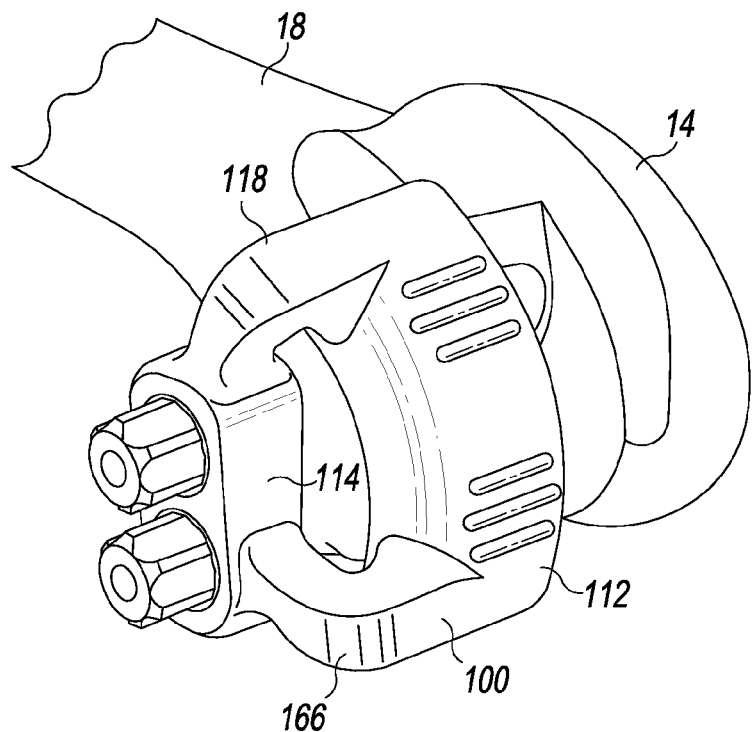
FIG. 18 is a medial perspective view of the primary femoral prosthetic component attached to a distal end of a patient's femur and the customized patient-specific femoral pin guide positioned thereon.
Figure 19:
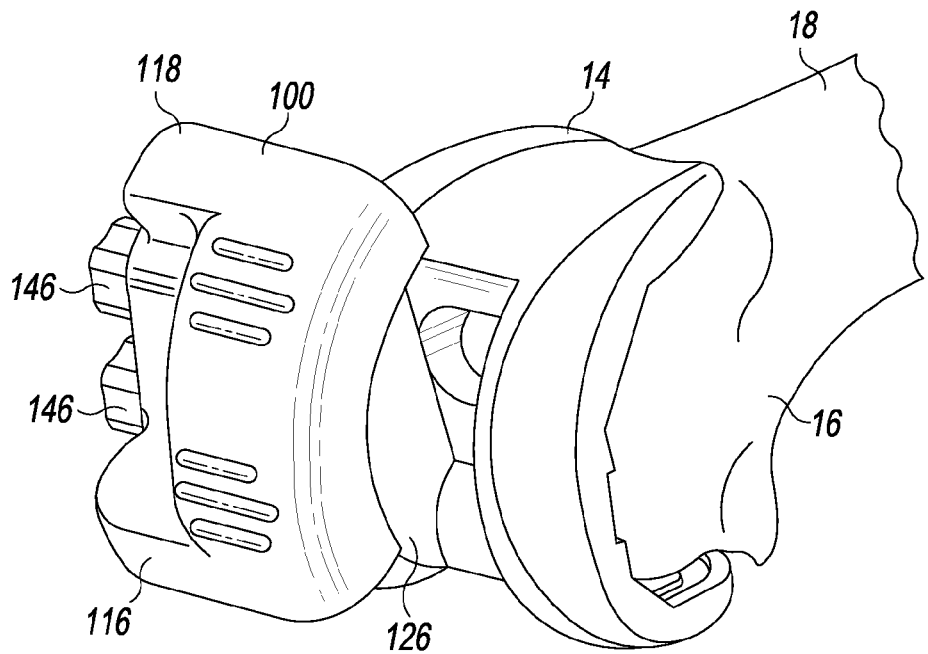
FIG. 19 is a lateral perspective view of the primary femoral prosthetic component attached to a distal end of a patient's femur and the customized patient-specific femoral pin guide positioned thereon.

As shown in FIGS. 18-19, the assembled customized patient-specific pin guide 100 is then coupled to the primary femoral prosthetic component 14 on the distal end 16 of the patient's femur 18. Because the prosthesis-engaging surface 120 of the pin guide 100 includes the negative contour 124, the pin guide 100 is coupled to the primary femoral prosthetic component 14 (and hence the patient's femur 18) in a preplanned, unique position and orientation. As shown in FIG. 19, the medial condyle 126 of the primary femoral component 14 is captured within the main body 112 of the pin guide 100. When so coupled, the arms 116, 118 extend around the distal end 16 of the patient's femur 18 to position the support body 114 on the medial side of the patient's femur 18. As shown in FIG. 18, the elongated bores 148 of the drill bushings 146 extend in the medial/lateral direction away from the medial surface of the patient's femur 18.

Figure 20:
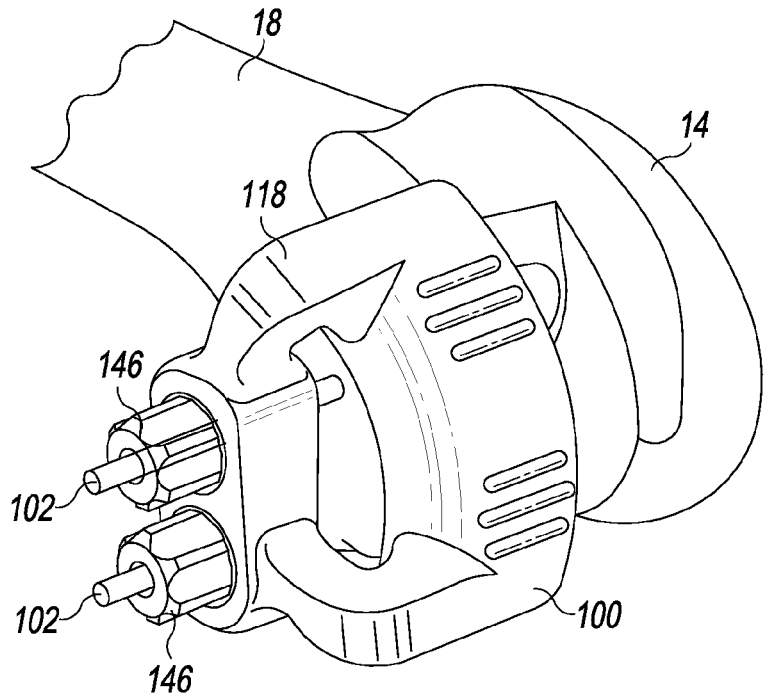
FIG. 20 is a view similar to FIG. 18 showing a pair of guide pins installed in the patient's femur.

The surgeon then installs the guide pins 102. To do so, the surgeon first drills pilot holes in the patient's femur by advancing a drill (not shown) through the guide bore 148 of each of the drill bushings 146. The surgeon then inserts a guide pin 102 through the guide bore 148 of each of the drill bushings 146 and into the drilled pilot holes. As shown in FIG. 20, the guide pins 102 are installed in the patient's femur in customized, patient-specific locations created by use of the customized, patient-specific pin guide 100. It should be appreciated that if the guide pins 102 are self-tapping pins, pre-drilling of the patient's femur is not necessary.

Figure 21:
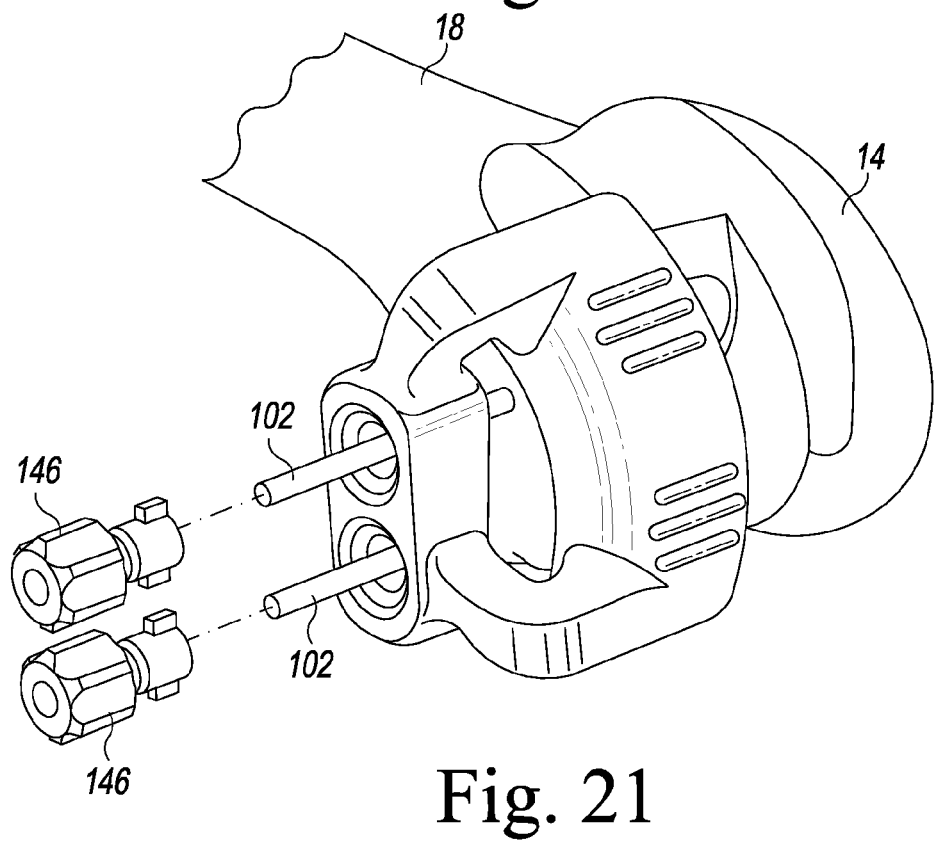
FIG. 21 is a view similar to FIG. 20 showing the drill bushings removed from the customized patient-specific femoral pin guide.

As shown in FIG. 21, once the guide pins 102 are installed in the patient's femur 18 in the customized, patient-specific locations by use of the pin guide 100, the drill bushings 146 are removed. Specifically, the surgeon first grips the head 150 of one of the removable drill bushing 146 and rotates it in the direction opposite the rotation during installation. The surgeon rotates the head 150 to a position in which the tabs 164 are aligned with the channels 158. Once the tabs 164 are aligned in such a manner, the post 152 of the removable drill bushing 146 may be removed from the guide hole 144, thereby disassembling the removable drill bushing 146 from the pin guide 100. The surgeon then removes the other drill bushing 146 from the pin guide's other guide hole 144 in a similar manner. In the illustrative embodiment, the drill bushings 146 are not disposed of, but rather may be retained and sterilized for use in a subsequent surgical procedure in combination with a customized patient-specific pin guide 100 that has been fabricated for another patient.

Figure 22:
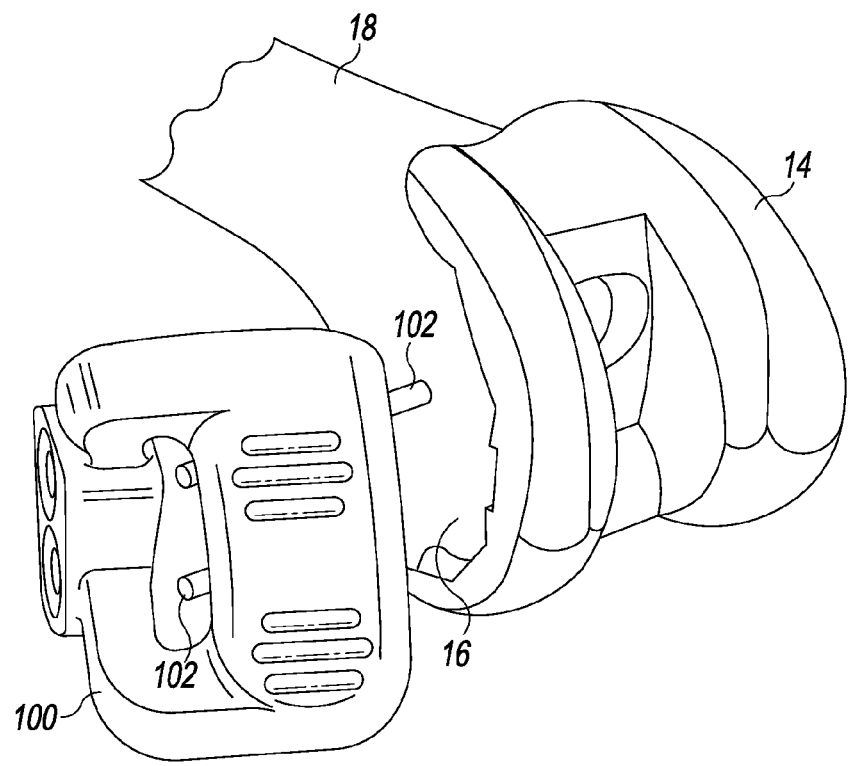
FIG. 22 is a view similar to FIG. 21 showing the customized patient-specific femoral pin guide detached from the primary femoral prosthetic component and the patient's femur and the pair of guide pins installed in the patient's femur.
Figure 23:
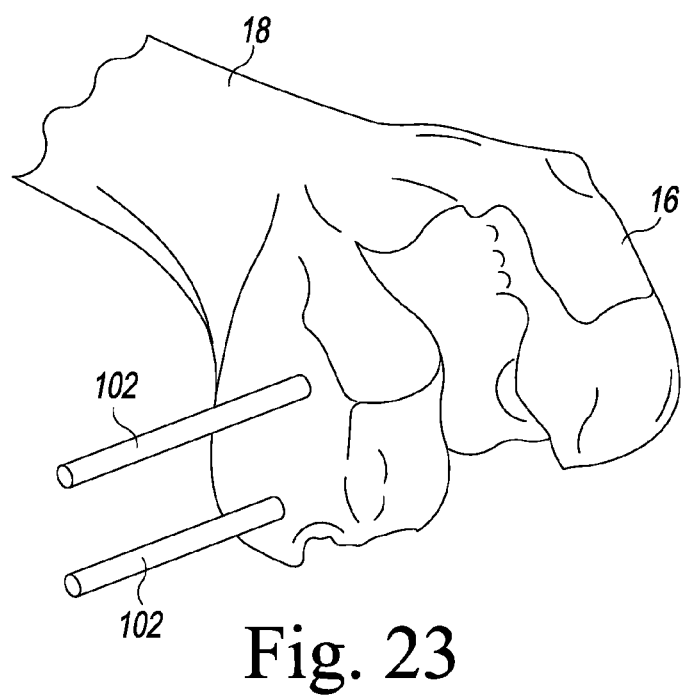
FIG. 23 is a view similar to FIG. 22 showing the pair of custom-located guide pins installed in the patient's femur.
Figure 24:
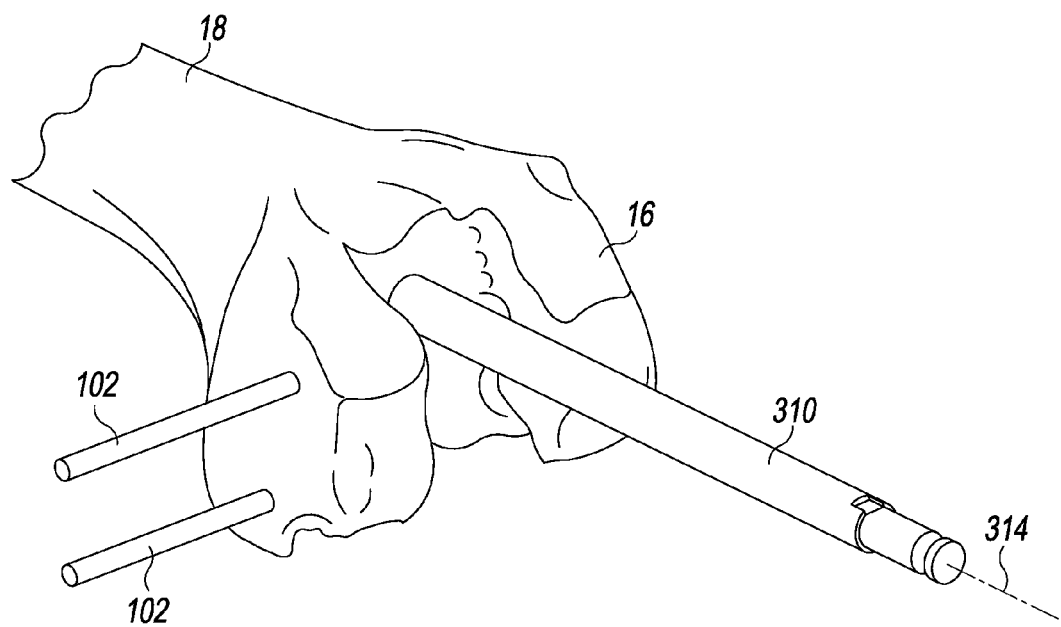
FIG. 24 is a medial perspective view of the patient's femur showing an intramedullary shaft inserted therein.

As shown in FIGS. 22 and 23, with the drill bushings 146 removed, the pin guide 100 is then de-coupled and removed from the primary femoral component 14 and hence the patient's femur 18. In doing so, the guide pins 102 are left behind in the patient's femur 18 in the customized, patient-specific locations created by use of the pin guide 100. The surgeon may then insert a canal reaming tool (not shown) or broach (not shown) into the distal end 16 of the patient's femur 18 to prepare medullary canal. One exemplary method of performing those operations is shown and described in SIGMA® Revision and M.B.T. Revision Tray Surgical Technique published 2008 by DePuy Orthopaedics, Inc., which is expressly incorporated herein by reference. The surgeon may then position an intramedullary shaft 310 in the medullary canal as shown in FIG. 24.

Figure 25:
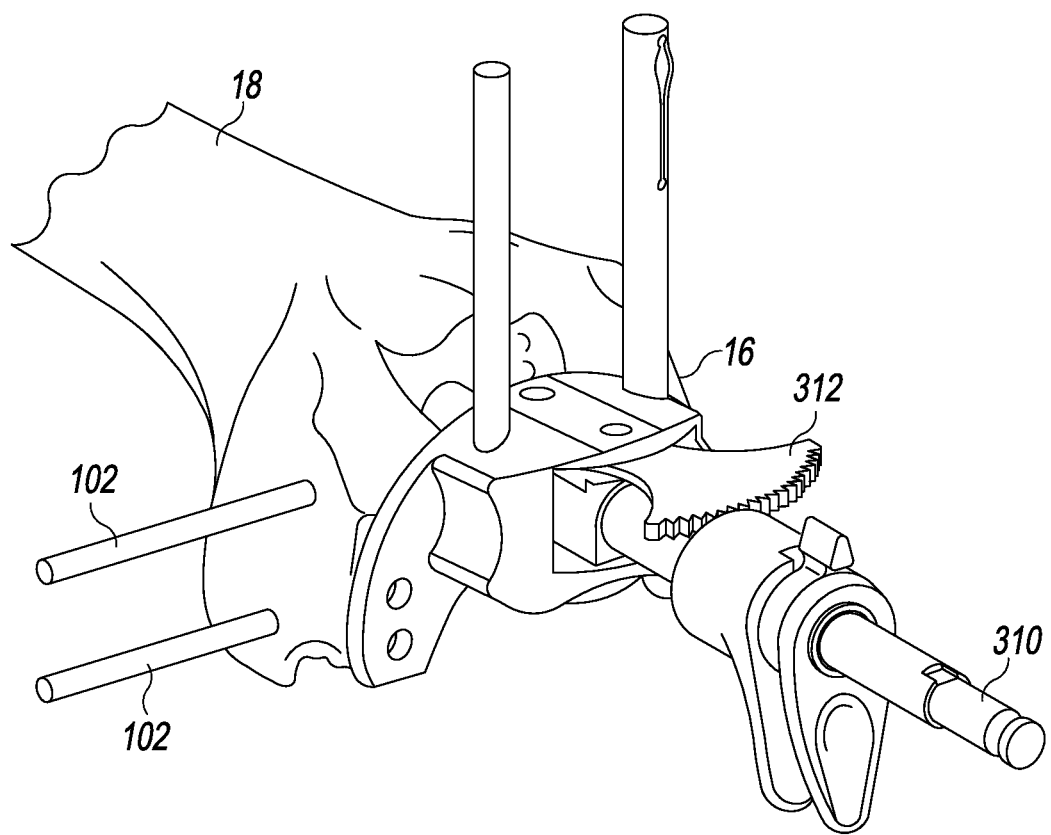
FIG. 25 is a view similar to FIG. 24 showing a femoral locating device attached to the intramedullary shaft of FIG. 24.
Figure 26:
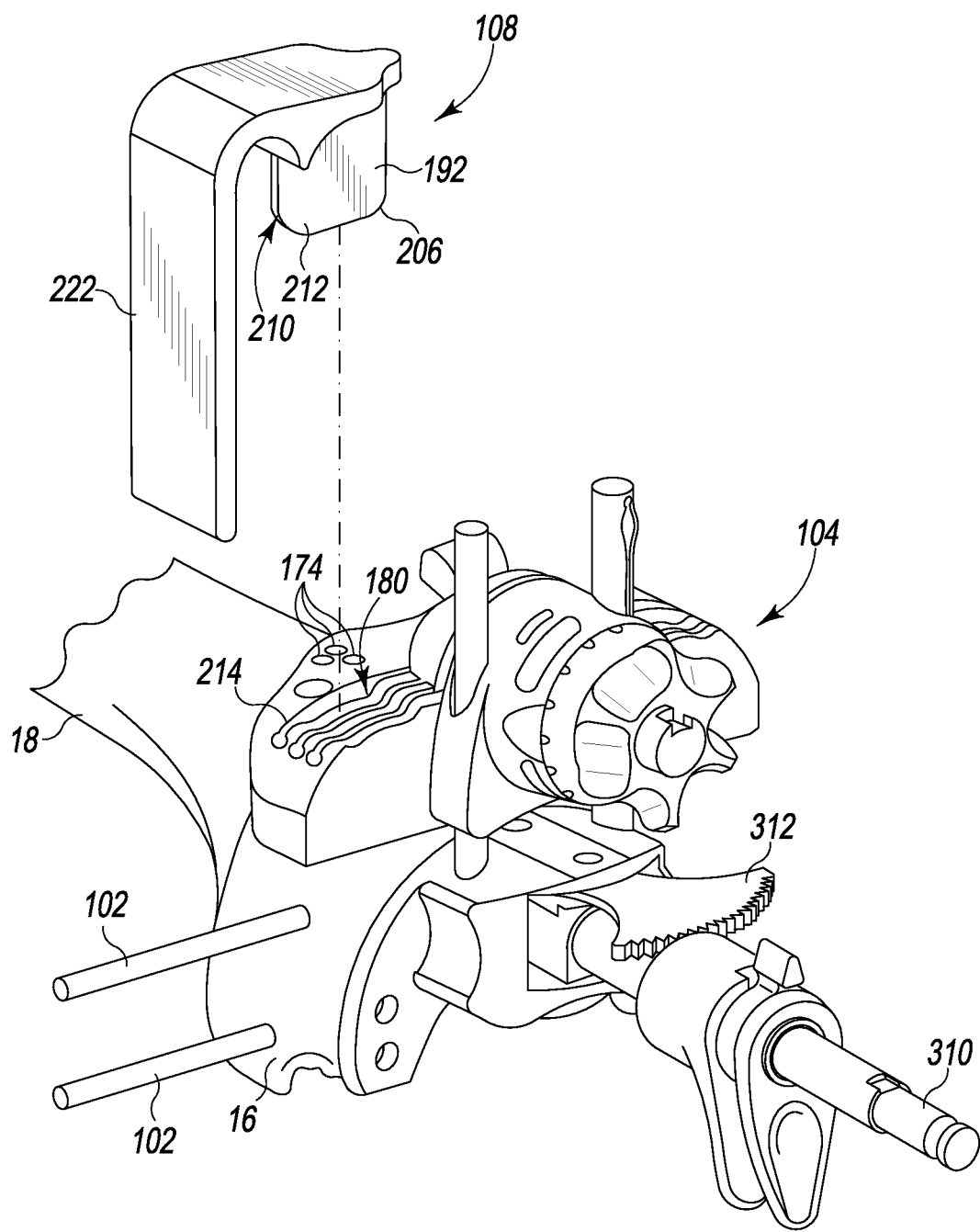
FIG. 26 is a view similar to FIG. 25 showing the distal cutting guide block of FIG. 11 attached to the femoral locating device and the alignment bracket of FIGS. 11-14 aligned with one of the distal cutting guides.

As shown in FIG. 25, the surgeon may then attach a femoral locating device 312 to the shaft 310. Using the surgical plan developed with algorithm 10, the surgeon may use the locating device 312 to set the preplanned valgus angle and right/left knee indication. The surgeon may then position the distal cutting block 104 on the locating device 312, as shown in FIG. 26.

Figure 27:
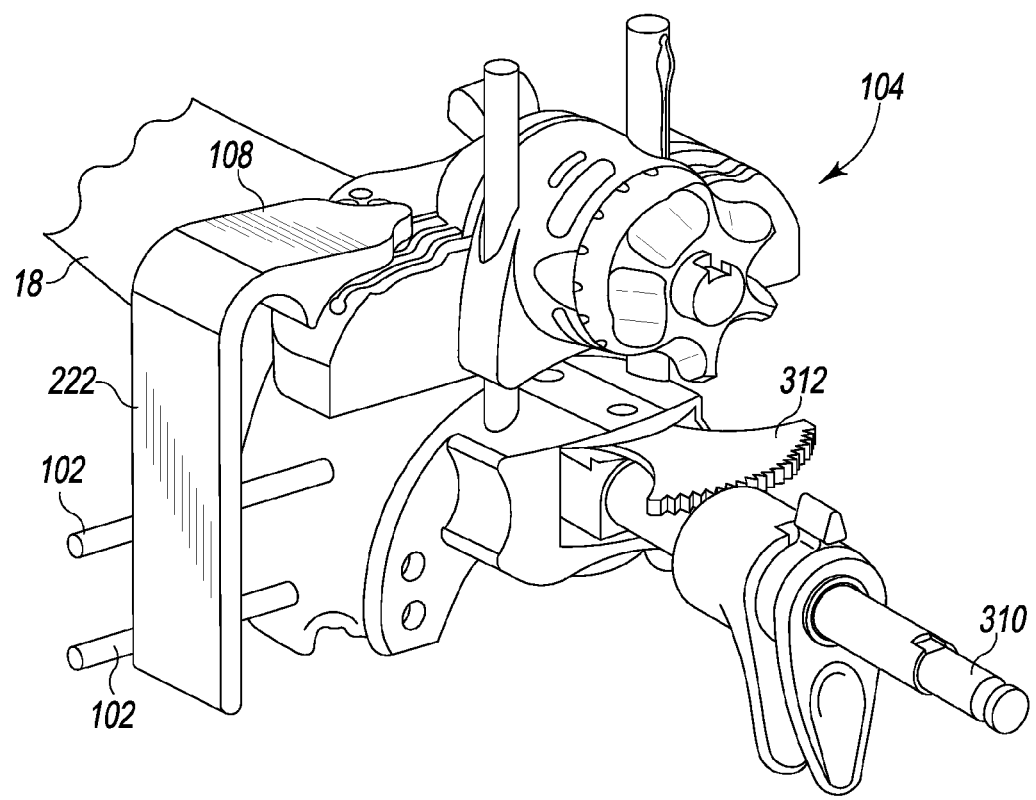
FIG. 27 is a view similar to FIG. 26 showing the alignment bracket secured to the distal cutting guide block.

The surgeon may attach the alignment bracket 108 to the distal cutting block 104 before or after the cutting block 104 is positioned on the locating device 312. To do so, the mounting flange 192 is aligned with the desired cutting guide of the distal cutting block 104 as shown in FIG. 26. In the illustrative embodiment, the desired cutting guide is the cutting guide 180, which is the "+8 mm" setting of the distal cutting block 104. The alignment bracket 108 may then be moved toward the cutting block 104 to advance the tip 206 of the mounting flange 192 into the anterior opening 214 of the cutting guide 180 and position the anterior side wall 172 of the block 104 in the negative contour 202 of the bracket 108. As described above, the surfaces 210, 212 of the mounting flange 192 engage the walls of the cutting guide 180 to retain the flange 192 therein, thereby securing the alignment bracket 108 to the cutting block 104, as shown in FIG. 27.

Figure 28:
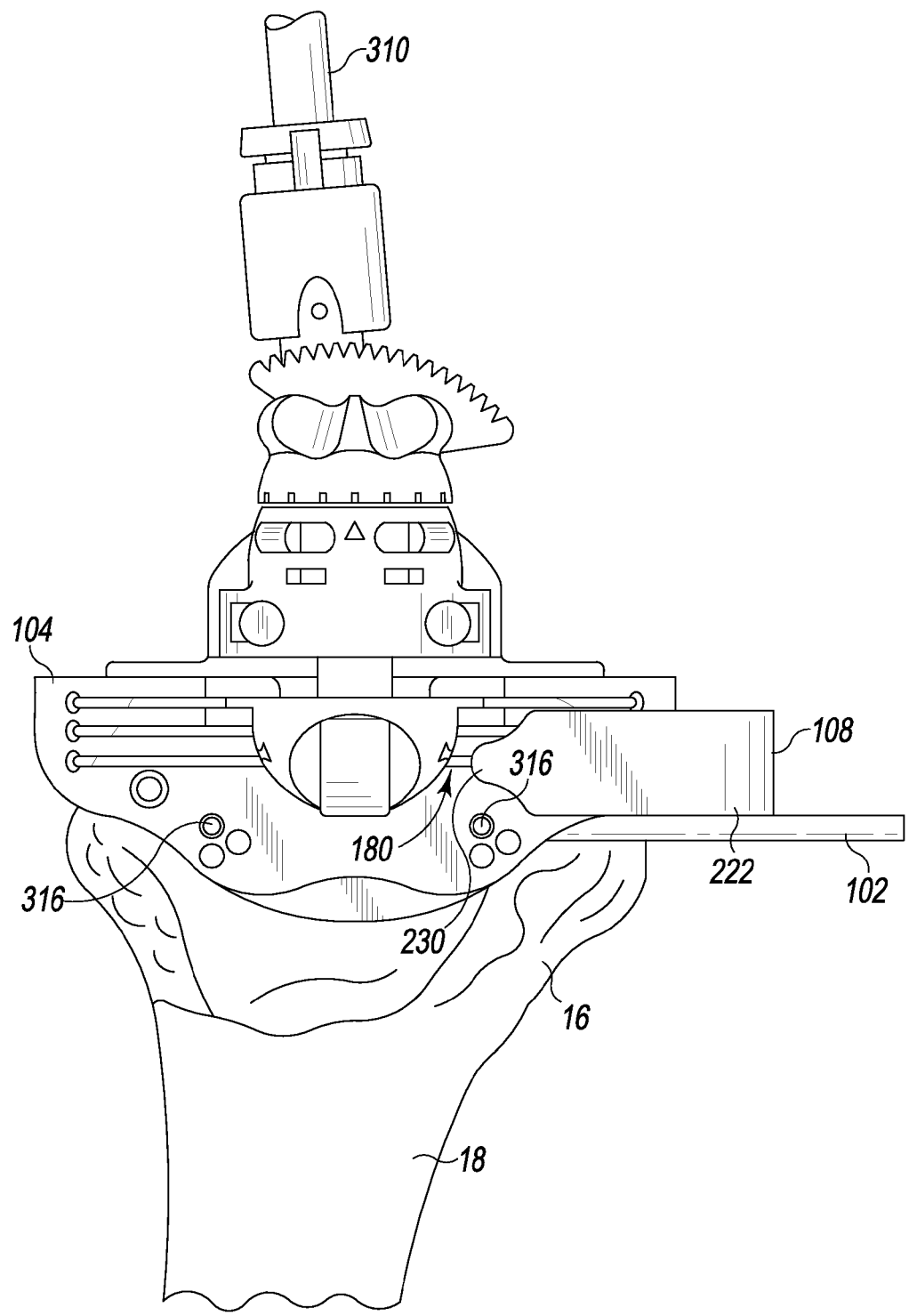
FIG. 28 is an anterior elevation view of the patient's femur showing the alignment bracket secured to the distal cutting guide block and engaged with the custom-located guide pins.

The intramedullary shaft 310 extends along an anatomical axis 314 of the patient's femur 18. The locating device 312 (and hence the cutting block 106) may then be advanced along the shaft 310 (and hence the axis 314) toward the distal end 16 of the patient's femur 18. When the lower surface 222 of the alignment bracket 108 engages the custom-located guide pins 102, the distal cutting block 104 is located in the preplanned position relative to the patient's femur 18. As shown in FIG. 28, additional guide pins 316 may be advanced into the guide pin holes 174 of the distal cutting block 104 to secure the block 104 to the distal end 16 of the patient's femur 18.

When the block 104 is secured to the femur 18, the alignment bracket 108 may be removed. The surgeon may use the distal cutting block 104 to resect the distal surfaces of the patient's femur 18. To do so, the surgeon advances a bone saw blade into the cutting guide 180 and cuts the femur. As described above, the amount of bone removed with the distal cutting block 104 determines the final location or elevation of the joint line of the revision orthopaedic prosthesis. If need be, the surgeon may reposition the cutting block 104 on the guide pins 316 by using a different pair of guide pin holes to perform a second cut to remove more bone. Once the distal surfaces of the patient's femur 18 have been resected, the surgeon may then continue with the surgical procedure.

Figure 29:
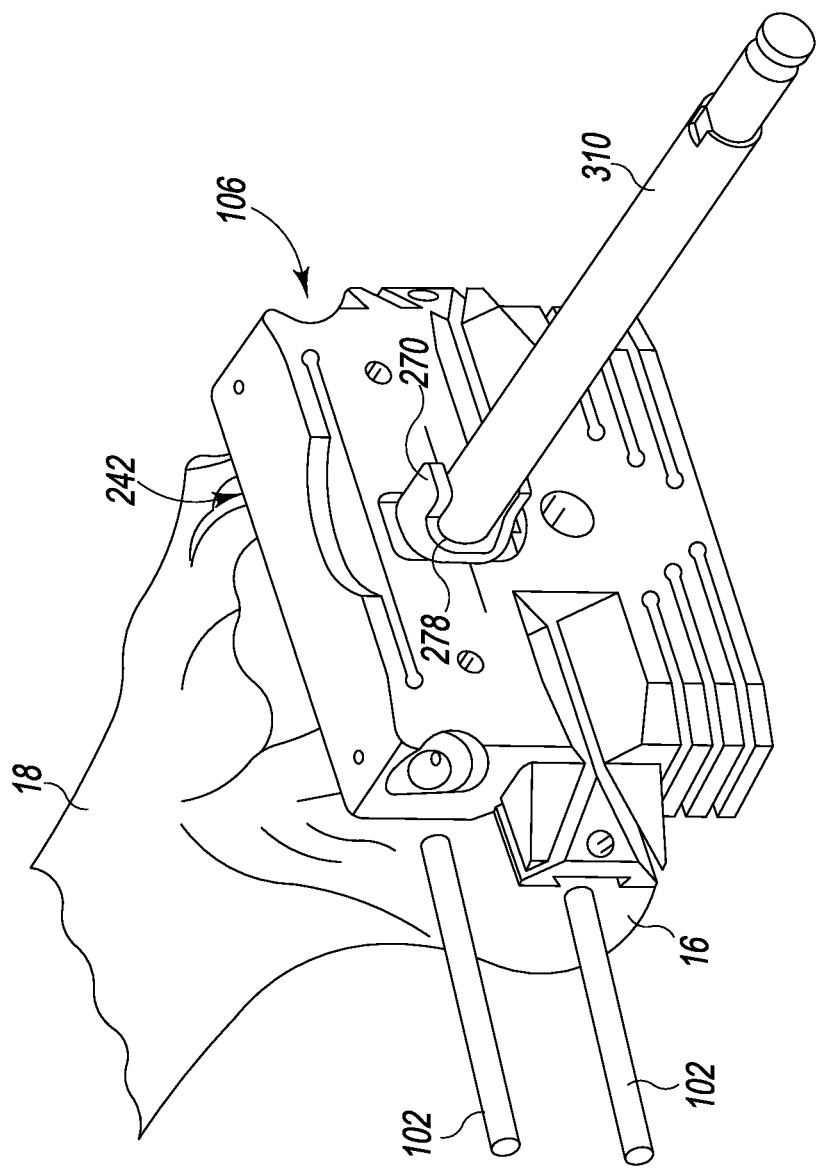
FIG. 29 is a medial perspective view showing the 4-in-1 cutting guide block of FIG. 15 engaged with the distal end of the patient's femur and the intramedullary shaft.

As shown in FIG. 29, the locating device 312, the distal cutting block 104, and the additional guide pins 316 may be removed after the distal cut is performed. In doing so, the custom-located guide pins 102 are left behind in the patient's femur 18. The surgeon may then position the 4-in-1 cutting block 106 on the intramedullary shaft 310. To do so, the surgeon aligns the bore 278 of the block's bushing 270 with the shaft 310 and advances the block 106 toward the patient's femur 18 until the bone-engaging surface 242 contacts the distal surfaces of the patient's femur 18.

Figure 30:
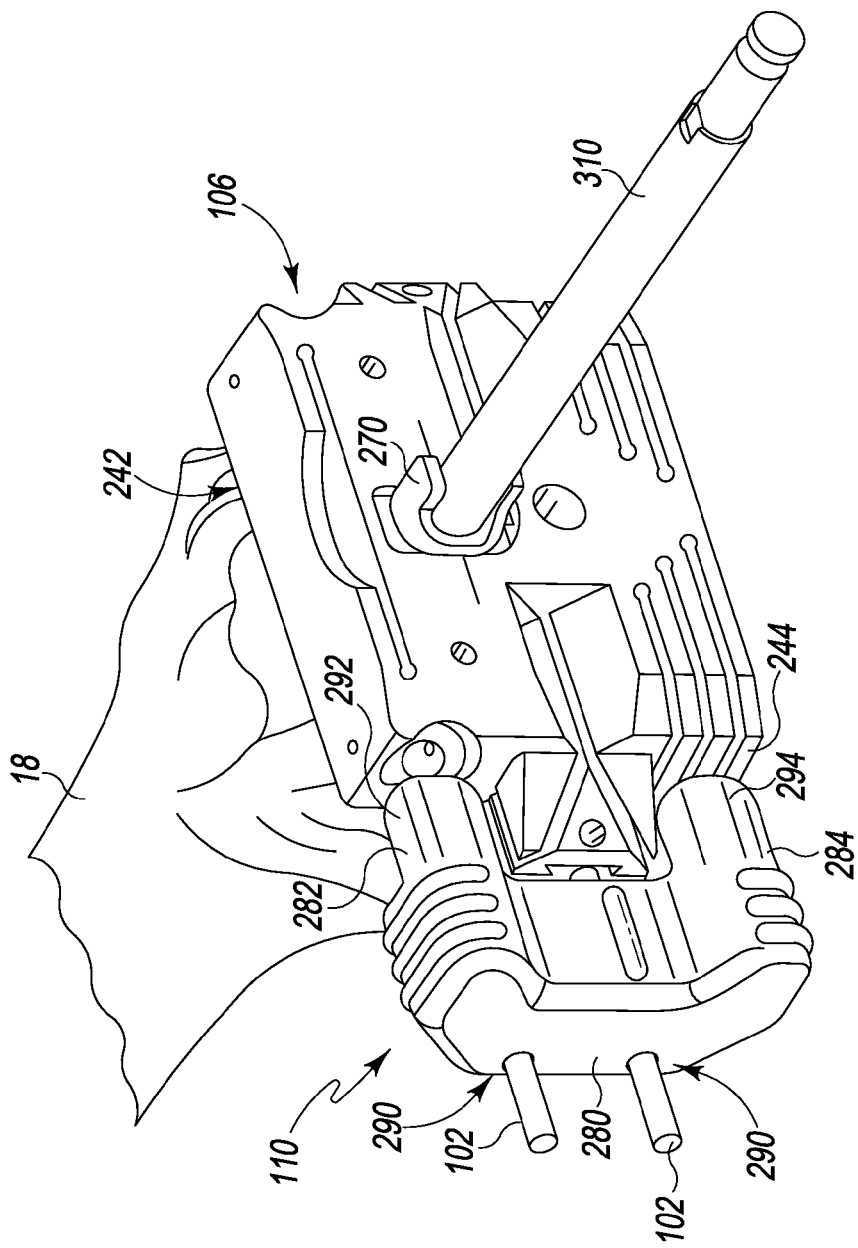
FIG. 30 is a view similar to FIG. 29 showing the customized patient-specific alignment guide of FIGS. 15 and 16 engaged with the 4-in-1 cutting guide block and the custom-located guide pins.

The surgeon may install the alignment guide 110 on the custom-located guide pins 102 by aligning the guide pin holes 290 with the guide pins 102 and advancing the body 280 of the guide 110 over the guide pins 102. As shown in FIG. 30, the alignment guide 110 is advanced along the guide pins 102 to engage the tips 292, 294 of the posts 282, 284 with the medial side wall 244 of the cutting block 106. The engagement between the tips 292, 294 of the guide 110 and the side wall 244 of the block 106 causes the block 106 to rotate about the shaft 310 in the direction indicated by arrow 318 in FIG. 31. The side wall 244 is thereby brought flush with the block-engaging surfaces 296, 298 of the tips 292, 294. The amount of rotation of the block 106 about the shaft 310 corresponds to the preplanned femoral rotation of the revision femoral component.

Figure 31:
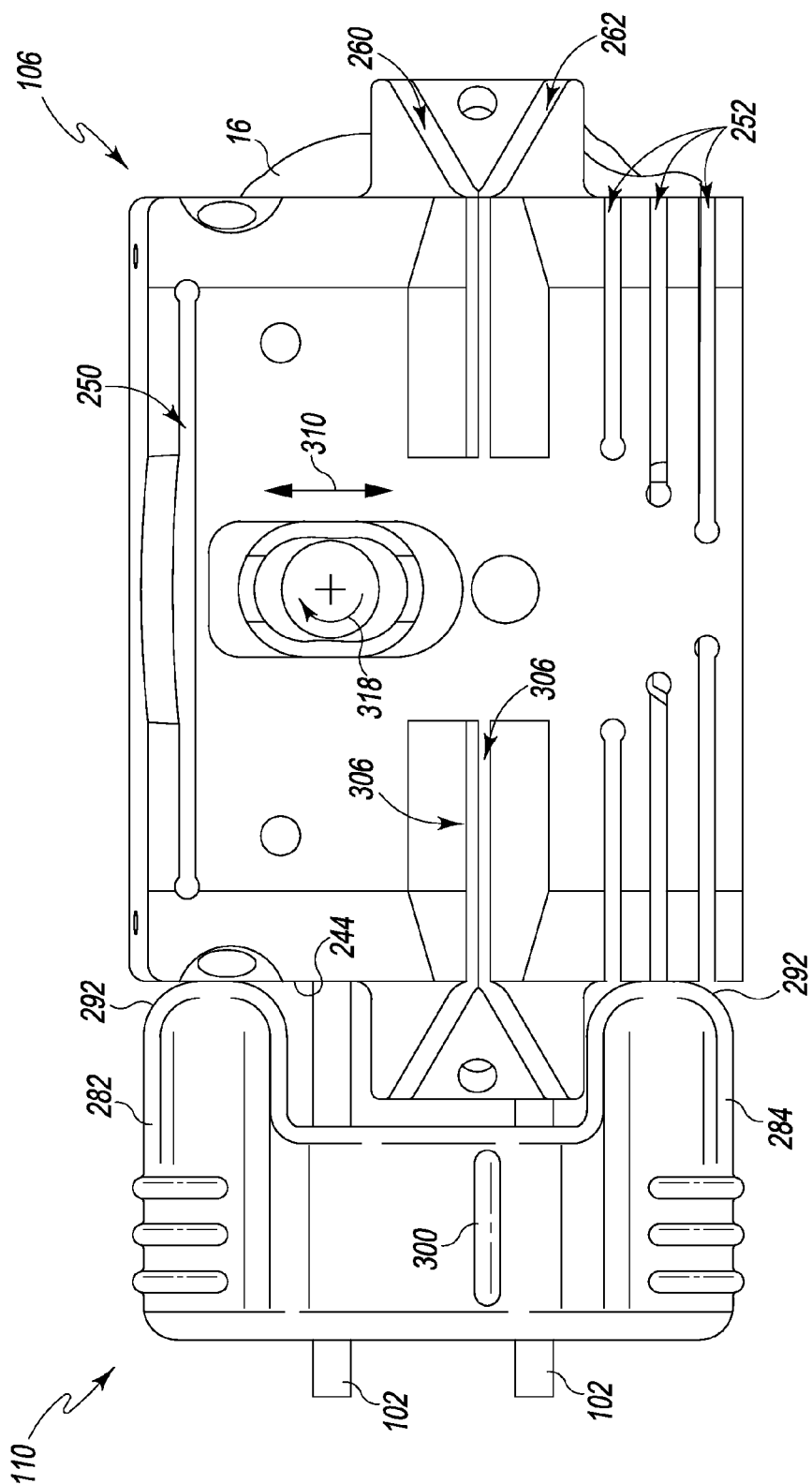
FIG. 31 is a distal elevation view of the patient's femur showing the alignment guide engaged with the 4-in-1 cutting guide block and the custom-located guide pins.
Figure 32:
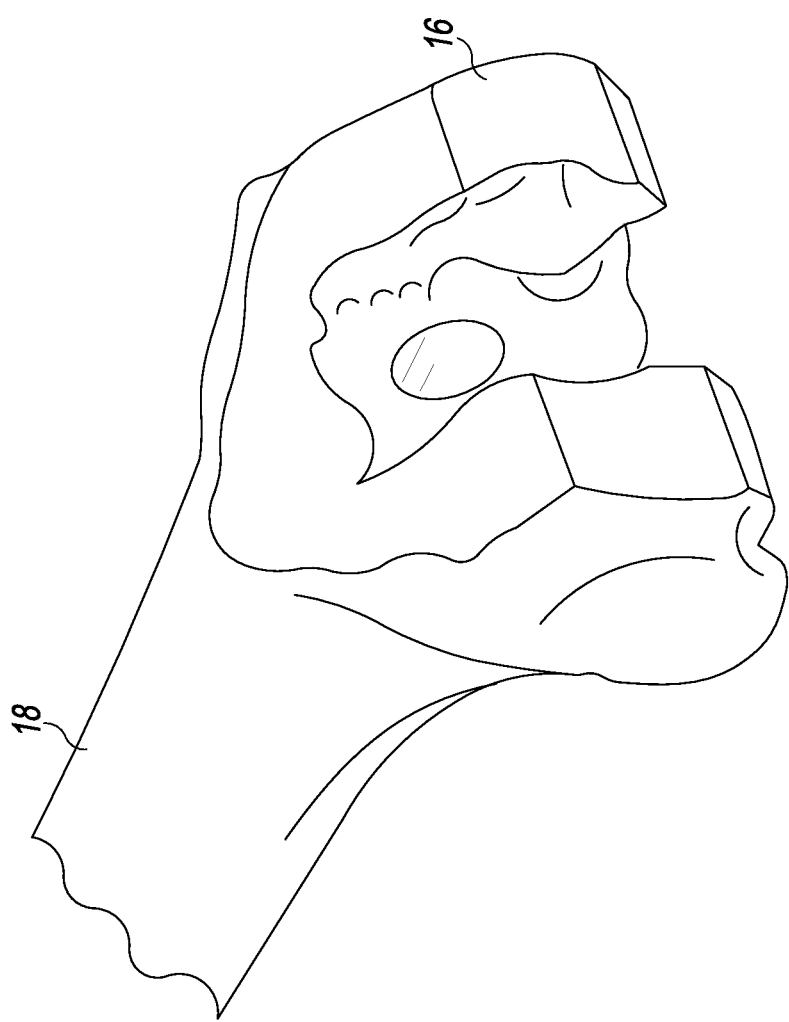
FIG. 32 is a medial perspective view of the surgically-prepared distal end of the patient's femur.

The surgeon may then move the 4-in-1 cutting block 106 relative to the shaft 310 (and hence the femur 18) in the anterior/posterior direction indicated by arrow 320 in FIG. 31. To do so, the surgeon grasps the block 106 and moves block 106 relative to the bushing 270. When the anterior openings 306 of the chamfer cutting guides 260, 262 with the marking 300 of the alignment guide 110, the cutting block 106 is located in the preplanned anterior-posterior position and may be locked into position. The alignment guide 110 may then be removed, and the surgeon may use the cutting block 106 to resect the anterior, posterior, and chamfer surfaces of the patient's femur 18. To do so, the surgeon advances a bone saw blade into the anterior cutting guide 248, the anterior chamfer guide 260, the posterior chamfer guide 262, and the desired posterior cutting guide 252 and cuts the femur. Once the distal end 16 of the patient's femur 18 has been resected as shown in FIG. 32, the surgeon may then continue with the surgical procedure to implant the revision orthopaedic prosthesis.

Figure 33:
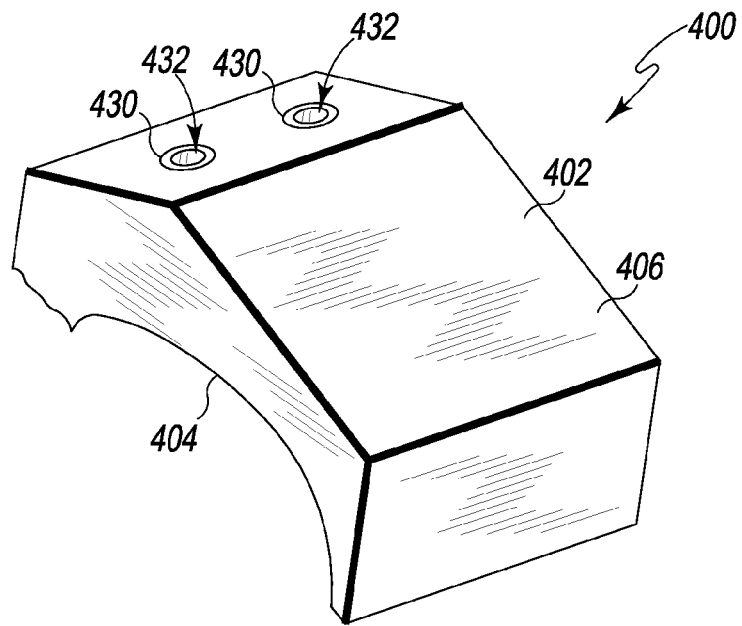
FIG. 33 is a perspective view of another embodiment of a customized patient-specific femoral pin guide.
Figure 34:
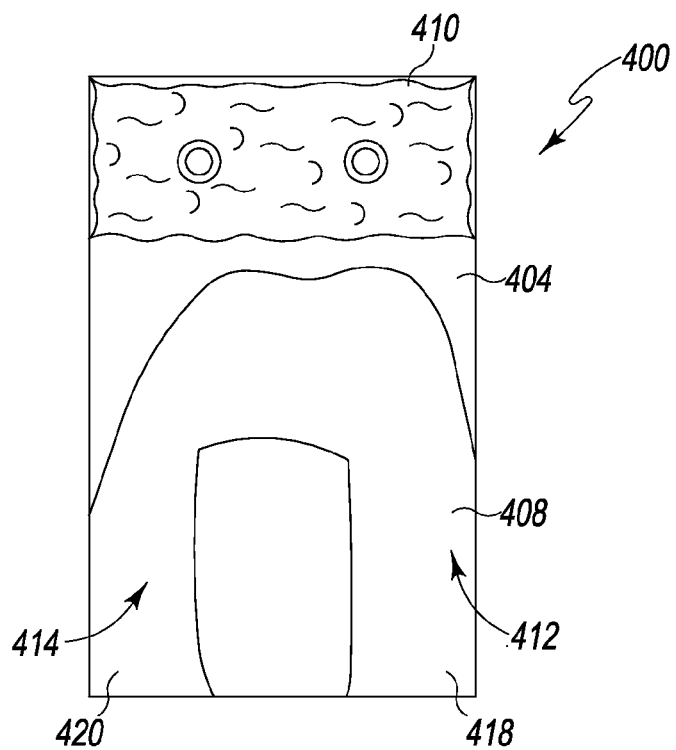
FIG. 34 is a posterior elevation view of the customized patient-specific femoral pin guide of FIG. 33.
Figure 35:
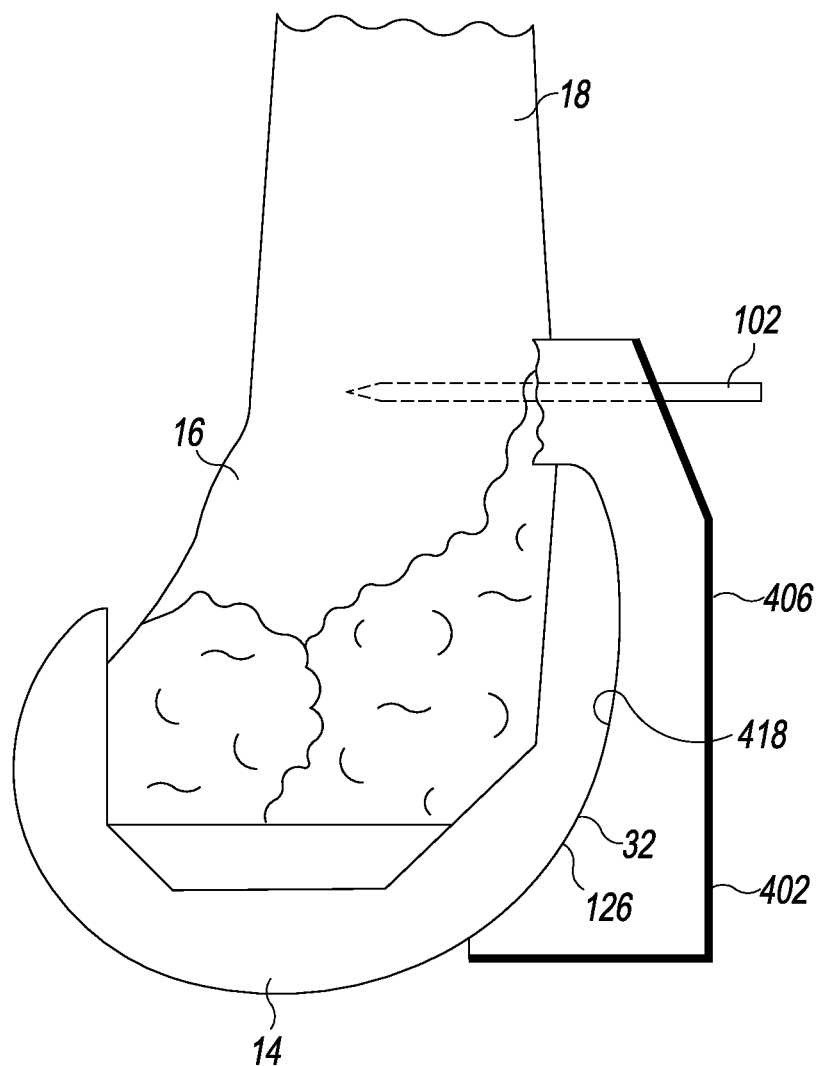
FIG. 35 is a medial side elevation view of the customized patient-specific femoral pin guide of FIGS. 33-34 attached to the patient's femur.

Referring now to FIGS. 33-35, another embodiment of a femoral pin guide (hereinafter pin guide 400) is shown. Like the pin guide 100, the pin guide 400 is configured to be coupled to the distal end 16 of the patient's femur 18 and the primary femoral prosthetic component 14 of the primary knee prosthesis 12. The femoral pin guide 400 is used to install a pair of guide pins 102 in a location on the femur 18 that has been preplanned and customized for that particular patient. In the illustrative embodiment, the pin guide 400 is configured such that the guide pins 102 are inserted into the anterior side of the distal end 16 of the patient's femur 18. The femoral pin guide 400 is devoid of a cutting guide; as such, like the pin guide 100, other cutting blocks are required to resect and shape the distal end 16 of the patient's femur 18 to receive a revision femoral prosthetic component.

As shown in FIG. 33, the pin guide 400 includes a body 402 configured to engage the primary femoral prosthetic component 14 of the primary knee prosthesis 12. The pin guide 400 may be formed from a material such as a plastic or resin material. In some embodiments, the pin guide 400 may be formed from a photo-curable or laser-curable resin. In one particular embodiment, the pin guide 400 is formed from a Vero resin using a rapid prototype fabrication process. It should be appreciated that in other embodiments the pin guide 400 may be formed from other materials in other embodiments. For example, in another particular embodiment, the pin guide 400 is formed from a polyimide thermoplastic resin, such as an Ultem resin. In the illustrative embodiment described herein, the pin guide 400 is embodied as a monolithic structure.

The body 402 of the pin guide 400 includes a posterior surface 404 and an outer surface 406 opposite the posterior surface 404. As shown in FIG. 34, the posterior surface 404 includes prosthesis-facing or engaging surface 408 and a bone-facing or engaging surface 410. The prosthesis-engaging surface 408 includes a negative contour 412 that is configured to receive a portion of a medial condyle 126 of the primary femoral component 14 having a corresponding contour and a negative contour 414 that is configured to receive a portion of a lateral condyle 416 (see, e.g. FIG. 37) of the primary femoral component 14 having a corresponding contour. In the illustrative embodiment, the negative contours 412, 414 of pin guide 400 include curved inner surfaces 418, 420, respectively, that are shaped to match the curved condyle surfaces 32, 34 of the medial condyle 126 of the lateral condyle 416.

The bone-engaging surface 410 of the pin guide 400 includes a negative contour 424 configured to receive a portion of the patient's femur 18 having a corresponding contour 426. In the illustrative embodiment, the negative contour 424 includes a unique plurality of depressions and ridges 428 that match a corresponding plurality of depressions and ridges of the corresponding contour 426 of the patient's femur 18. As such, the negative contour 424 of the bone-engaging surface 410, in conjunction with the negative contours 412, 414 of the prosthesis-engaging surface 408, permits the pin guide 100 to be positioned on the patient's femur 18 in a unique predetermined location and orientation, as shown in FIG. 35.

The pin guide 400 also has a pair of metallic bushings 430 that are secured to the body 402. As shown in FIGS. 33-35, each bushing 430 extends through the thickness of the body 402—that is, each bushing 430 extends through the pin guide's posterior surface 404 and outer surface 406. As shown in FIG. 35, each bushing 430 includes an elongated bore 432 that extends therethrough. The bore 432 is sized to receive a drill such that the patient's femur may be pre-drilled prior to installation of the guide pins 102. Each bore 432 is also sized to receive a corresponding guide pin 102, as shown in FIG. 35. It should be appreciated that in other embodiments the pin guide 400 may be configured for use with removable drill bushings similar to those described above in regard to the femoral pin guide 100.

The metallic components described herein may be secured to the polymer pin guide in a number of different manners. For example, the metallic components may be overmolded to the polymer guide or otherwise secured to it as part of the molding process of the guide. The metallic components may also be welded to the guide or secured to it with an adhesive. Other methods of securing the metallic components may also be employed.

Figure 36:
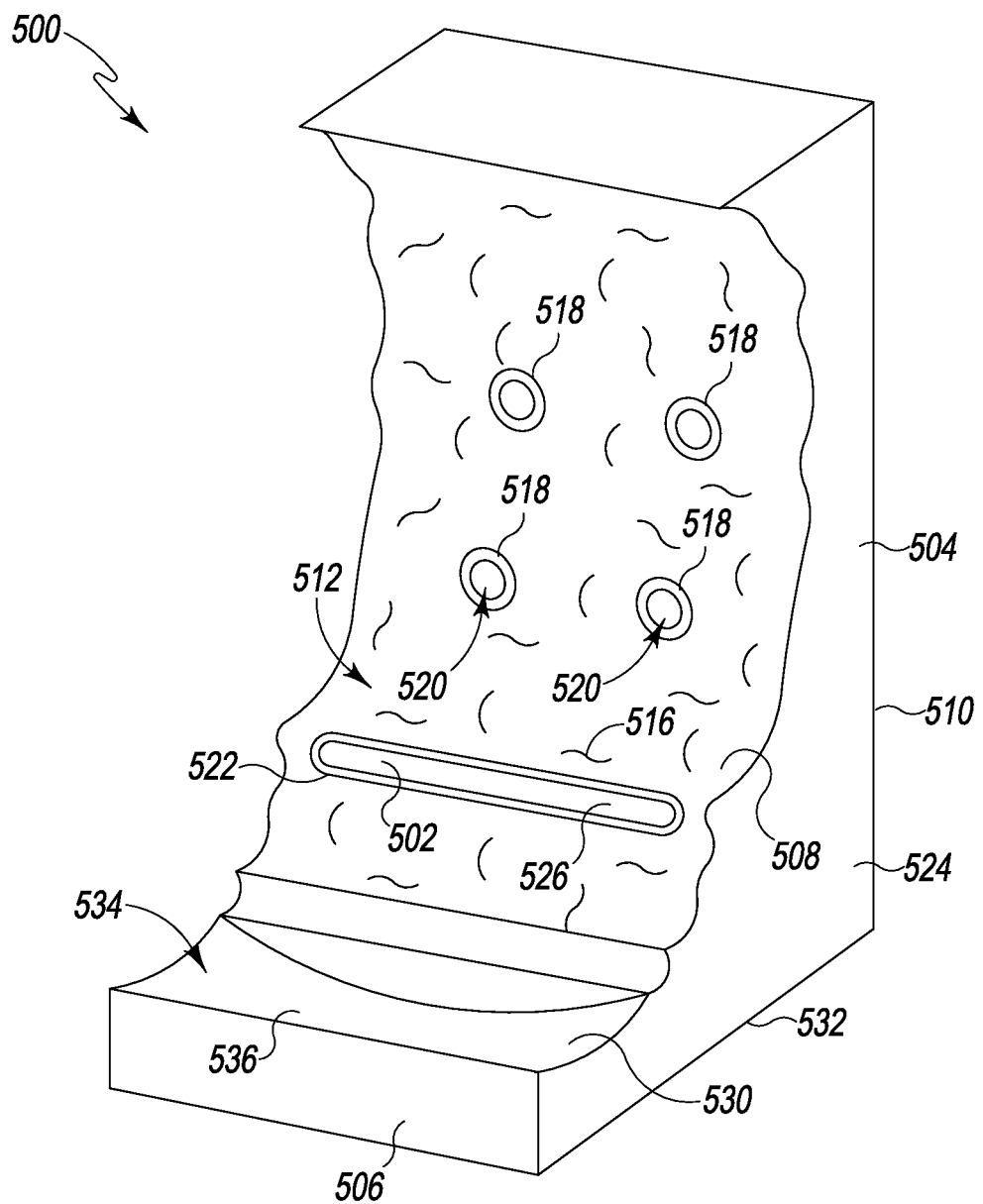
FIG. 36 is a perspective view of another embodiment of a customized patient-specific femoral pin guide including a distal cutting guide.
Figure 37:
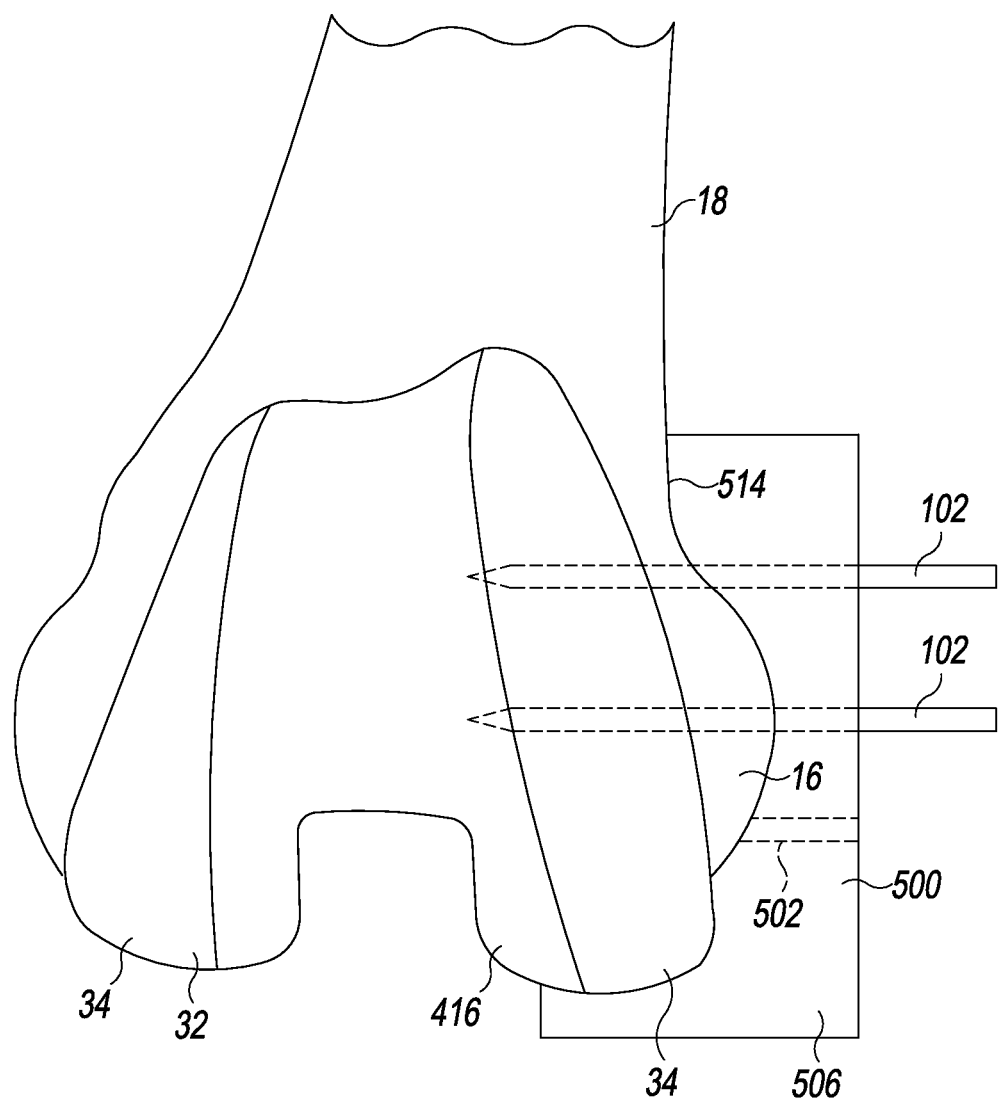
FIG. 37 is an anterior elevation view of the femoral pin guide of FIG. 36 attached to the patient's femur.

Referring now to FIGS. 36-37, another embodiment of a femoral pin guide (hereinafter pin guide 500) is shown. Like the pin guides 100 and 400, the pin guide 500 is configured to be coupled to the distal end 16 of the patient's femur 18 and the primary femoral prosthetic component 14 of the primary knee prosthesis 12. The femoral pin guide 500 is used to install a pair of guide pins 102 in a location on the femur 18 that has been preplanned and customized for that particular patient. In the illustrative embodiment, the pin guide 500 is configured such that the guide pins 102 are inserted into the lateral side of the distal end 16 of the patient's femur 18. As shown in FIG. 36, the femoral pin guide 500 includes a cutting guide 502 that may be used to resect the patient's femur 18.

As shown in FIG. 36, the pin guide 500 includes a body 504 configured to engage the patient's femur 18 and an arm 506 configured to engage the primary femoral prosthetic component 14 of the primary knee prosthesis 12. The pin guide 500 may be formed from a material such as a plastic or resin material. In some embodiments, the pin guide 500 may be formed from a photo-curable or laser-curable resin. In one particular embodiment, the pin guide 500 is formed from a Vero resin using a rapid prototype fabrication process. It should be appreciated that in other embodiments the pin guide 500 may be formed from other materials in other embodiments. For example, in another particular embodiment, the pin guide 500 is formed from a polyimide thermoplastic resin, such as an Ultem resin. In the illustrative embodiment described herein, the pin guide 500 is embodied as a monolithic structure.

The body 504 of the pin guide 500 includes a bone-facing or bone-engaging surface 508 and an outer surface 510 opposite the bone-engaging surface 508. The bone-engaging surface 508 of the pin guide 500 includes a negative contour 512 configured to receive a portion of the patient's femur 18 having a corresponding contour 514 (see FIG. 37). In the illustrative embodiment, the negative contour 512 includes a unique plurality of depressions and ridges 516 that match a corresponding plurality of depressions and ridges of the corresponding contour 514 of the patient's femur 18. The pin guide 500 also has a number of metallic bushings 518 that are secured to the body 504. As shown in FIGS. 36-37, each bushing 518 extends through the thickness of the body 504—that is, each bushing 518 extends through the pin guide's bone-engaging surface 508 and outer surface 510. As shown in FIG. 37, each bushing 518 includes an elongated bore 520 that extends therethrough. The bore 520 is sized to receive a drill such that the patient's femur may be pre-drilled prior to installation of the guide pins 102. Each bore 518 is also sized to receive a corresponding guide pin 102, as shown in FIG. 37. It should be appreciated that in other embodiments the pin guide 500 may be configured for use with removable drill bushings similar to those described above in regard to the femoral pin guide 100.

The body 504 has a cutting guide slot 522 formed near its distal end 524. The cutting guide slot 522 is an elongated slot extending in the anterior/posterior direction. The cutting guide slot 522 extends through the entire thickness of the body 504 and is thereby being open to both the bone-engaging surface 508 and the outer surface 510. As can be seen in FIG. 36, a metallic cutting guide 502 is secured within the cutting guide slot 522 of the body 504. The cutting guide 502 lines the cutting guide slot 522 and is embodied as a captured cutting guide (i.e., it is closed on all sides so as to capture a saw blade therein) including a substantially planar cutting guide surface 526. The cutting guide 502 is sized and shaped to receive the blade (not shown) of a surgical saw or other cutting instrument and orient the blade to resect the distal surface of the patient's femur during an orthopaedic surgical procedure. In the illustrative embodiment, the cutting guide 502 is positioned such that the surgeon may begin the resection with the primary femoral prosthetic component still attached the patient's femur.

As shown in FIG. 36, the arm 506 of the pin guide 500 includes a prosthesis-facing or engaging surface 530 and an outer surface 532 opposite the prosthesis-facing surface 530. The prosthesis-engaging surface 530 includes a negative contour 534 that is configured to receive a portion of the lateral condyle 416 of the primary femoral component 14 having a corresponding contour. In the illustrative embodiment, the negative contour 534 of pin guide 500 includes a curved inner surface 536 that is shaped to match the curved condyle surface 34 of the lateral condyle 416. As such, the negative contour 512 of the bone-engaging surface 508, in conjunction with the negative contour 534 of the prosthesis-engaging surface 530, permits the pin guide 500 to be positioned on the patient's femur 18 in a unique predetermined location and orientation, as shown in FIG. 37.

Referring now to FIGS. 38-41, the customized patient-specific instruments described herein may be embodied as a customized patient-specific tibial pin guide 600. The tibial pin guide 600 is configured to be coupled to the implanted primary tibial tray 22 and hence the patient's tibia 26. As described in greater detail below, the pin guide 600 is used to install a pair of guide pins 102 in a location on the tibia 26 that has been preplanned and customized for that particular patient. In the illustrative embodiment, the pin guide 600 is configured such that the guide pins 102 are inserted into the lateral side of the proximal end 24 of the patient's tibia 26. It should be appreciated that in other embodiments the pin guide 600 may be configured to insert the pins 102 into the medial side or anterior side of the patient's tibia 26. Like the femoral pin guide 100, the tibial pin guide 600 is devoid of a cutting guide; as such, other cutting blocks are required to resect and shape the distal end 16 of the patient's femur 18 to receive a revision tibial prosthetic component.

Figure 38:
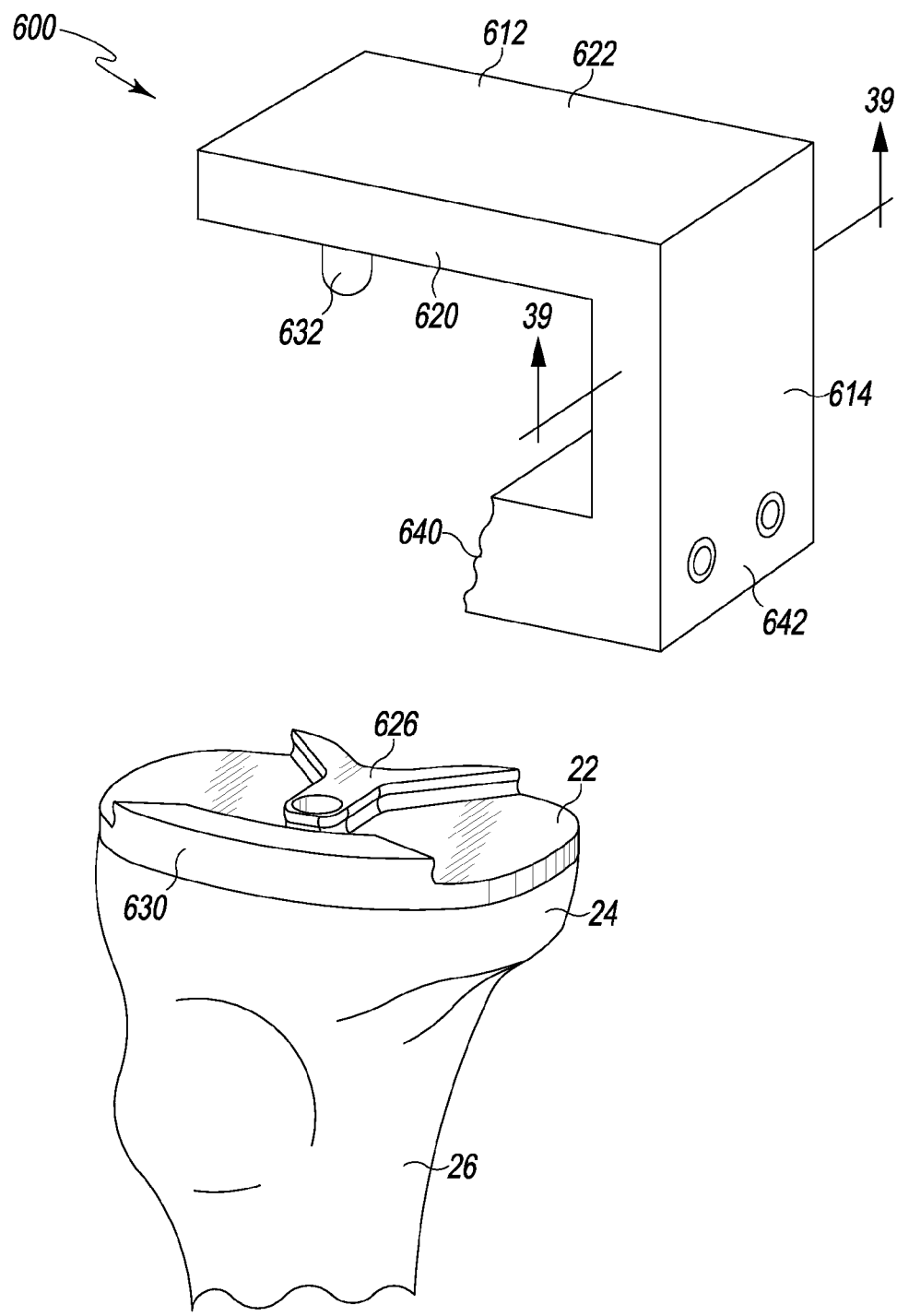
FIG. 38 is a perspective view of a customized patient-specific tibial pin guide and the primary tibial tray of FIG. 2 attached to the patient's tibia.

As shown in FIG. 38, the pin guide 600 includes a main body 612 configured to engage the primary tibial tray 22 of the primary knee prosthesis 12 and a support body 614 configured to be coupled to the lateral side of the patient's tibia 26. The pin guide 600 may be formed from a material such as a plastic or resin material. In some embodiments, the pin guide 600 may be formed from a photo-curable or laser-curable resin. In one particular embodiment, the pin guide 600 is formed from a Vero resin using a rapid prototype fabrication process. It should be appreciated that in other embodiments the pin guide 600 may be formed from other materials in other embodiments. For example, in another particular embodiment, the pin guide 600 is formed from a polyimide thermoplastic resin, such as an Ultem resin. In the illustrative embodiment described herein, the pin guide 600 is embodied as a monolithic structure.

Figure 39:
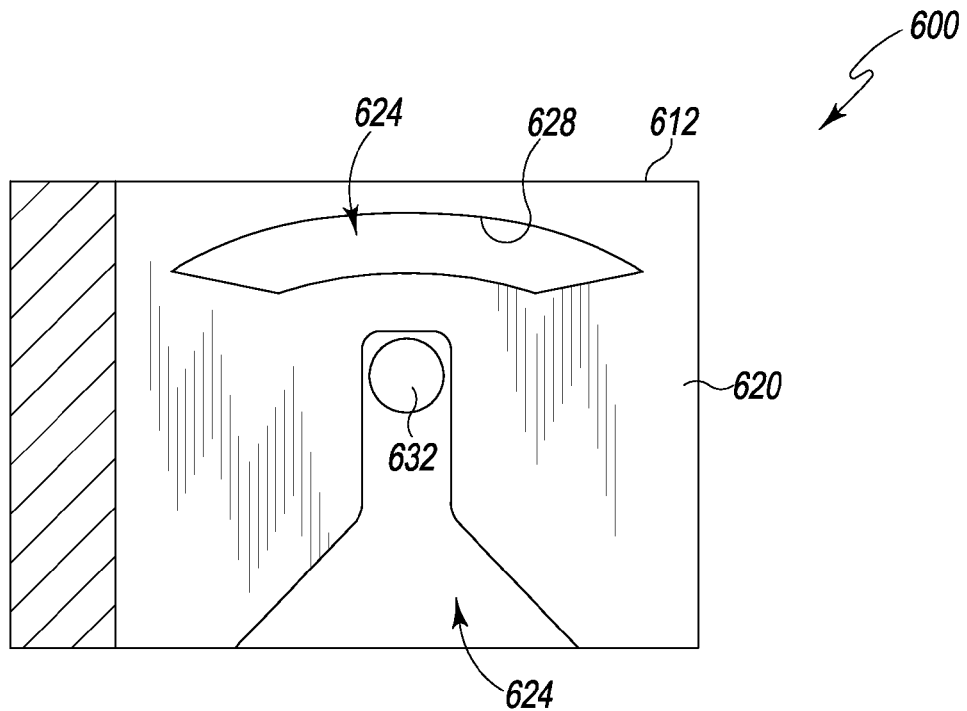
FIG. 39 is a fragmentary cross sectional view of the customized patient-specific tibial pin guide of FIG. 38 taken along the line 39-39 in FIG. 38, as viewed in the direction of the arrows.

The main body 612 of the pin guide 600 includes a prosthesis-engaging surface 620 and an outer surface 622 opposite the prosthesis-engaging surface 620. As shown in FIG. 39, the prosthesis-engaging surface 620 of the main body 112 includes a negative contour 624 that is configured to receive a portion of a platform 626 (see FIG. 38) of the primary tibial tray 22 having a corresponding contour. In the illustrative embodiment, the negative contour 624 of pin guide 600 includes a curved inner surface 628 that is shaped to match the convex curved surface 630 of the platform 626.

The pin guide 600 also includes a shaft 632 that is sized to be received in a stem bore 634 formed in the tibial tray 22. As shown in FIG. 38, the shaft 632 extends away from the main body 612. The shaft 632 is positioned such that the pin guide 600 is located in a unique position and orientation relative to the tibial tray 22.

Figure 40:
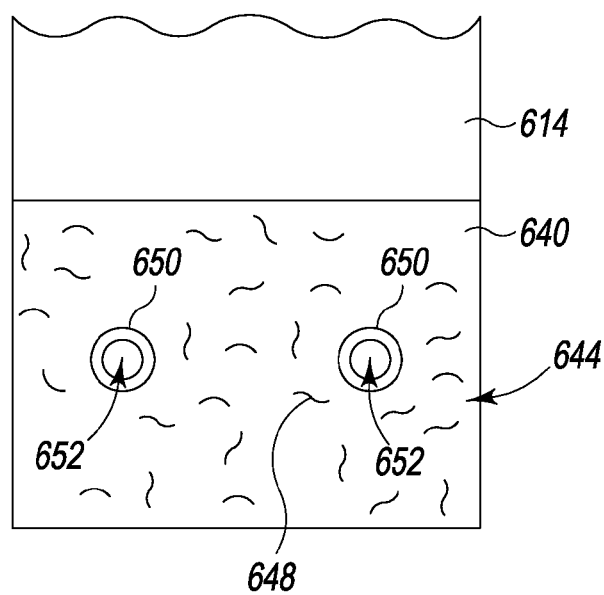
FIG. 40 is a fragmentary elevation view of the customized patient-specific tibial pin guide of FIG. 38.

The support body 614 of the pin guide 100 includes a bone-contacting or bone-facing surface 640 and an outer surface 642 opposite the bone-facing surface 640. As shown in FIG. 40, the bone-facing surface 640 includes a negative contour 644 configured to receive a portion of the patient's tibia 26 having a corresponding contour 646. In the illustrative embodiment, the negative contour 644 includes a unique plurality of depressions and ridges 648 that match a corresponding plurality of depressions and ridges of the corresponding contour 646 of the patient's tibia 26. The negative contour 644 of the bone-facing surface 640, in conjunction with the negative contour 624 of the prosthesis-engaging surface 620 and the shaft 632, permits the positioning of the pin guide 600 on the patient's tibia 26 in a unique predetermined location and orientation. In other embodiments, the negative contour 644 of the bone-facing surface 640 may be omitted.

It should be appreciated that in other embodiments the customized patient-specific pin guide may be configured to engage other portions of the primary tibial prosthetic component. For example, the pin guide might include a negative contour that is configured to receive a portion of the posterior edge of the primary tibial tray. In other embodiments, the pin guide might include a negative contour that is configured to engage the locking flange of the primary tibial tray.

Figure 41:
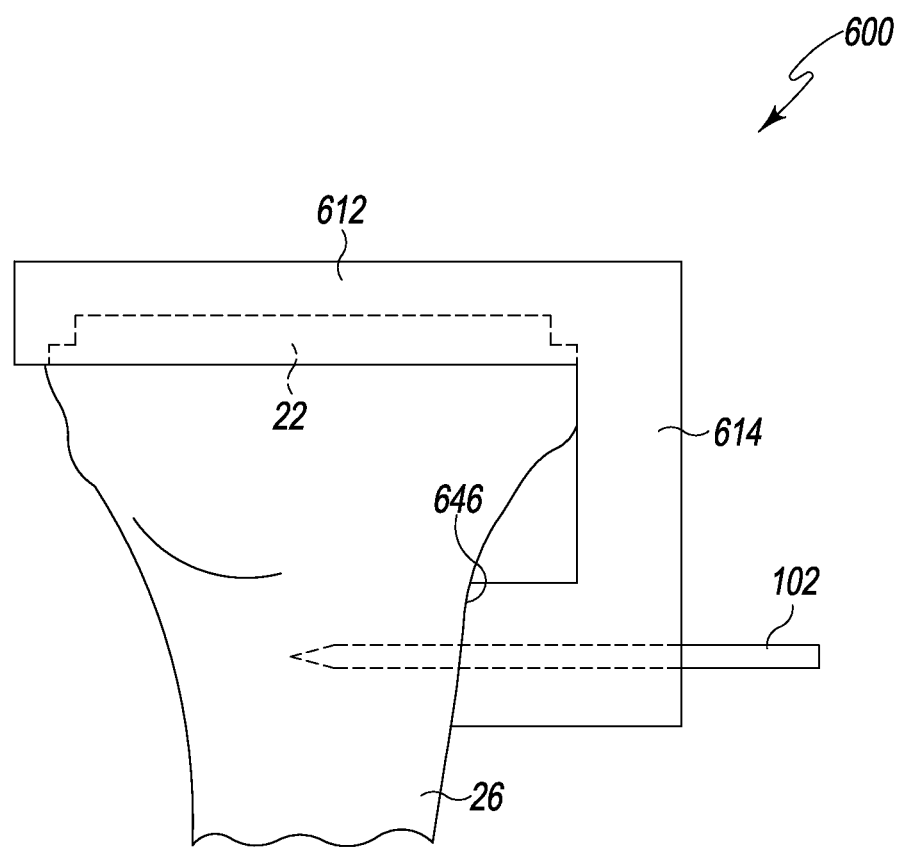
FIG. 41 is an anterior elevation view of the customized patient-specific tibial pin guide of FIG. 38 attached to the primary tibial tray.

The pin guide 600 also has a number of metallic bushings 650 secured to the body 614. Each bushing 650 extends through the thickness of the body 614—that is, each bushing 650 extends through the pin guide's bone-engaging surface 640 and outer surface 542. As shown in FIG. 41, each bushing 650 includes an elongated bore 652 that extends therethrough. The bore 652 is sized to receive a drill such that the patient's tibia may be pre-drilled prior to installation of the guide pins 102. Each bore 652 is also sized to receive a corresponding guide pin 102, as shown in FIG. 41. It should be appreciated that in other embodiments the tibial pin guide may be configured for use with removable drill bushings similar to those described above in regard to the femoral pin guide 100.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of performing an orthopaedic surgical procedure, the method comprising:

aligning a customized patient-specific guide block with a first prosthetic component implanted in an end of a bone of a patient, attaching the customized patient-specific guide block to the first prosthetic component in a unique location and orientation on the end of the bone, advancing a guide pin through a guide pin hole of the customized patient-specific guide block into the bone when the customized patient-specific guide block is positioned on the first prosthetic component, detaching the customized patient-specific guide block from the first prosthetic component and the end of the bone while leaving the guide pin secured to the bone, removing the first prosthetic component from the end of the bone, engaging an alignment block with the guide pin to position a cutting block on the bone, and resecting the end of the bone using the cutting block to guide the resection.

2. The method of claim 1, wherein positioning the customized patient-specific guide block on the first prosthetic component in the unique location and orientation includes engaging a customized prosthesis-specific negative contour of the customized patient-specific guide block with a corresponding contour of the first prosthetic component, the customized prosthesis-specific negative contour being shaped to match the corresponding contour of the first prosthetic component.

3. The method of claim 2, wherein:

the first prosthetic component includes a femoral prosthetic component having a pair of curved condyle surfaces configured to engage a bearing surface, and engaging the customized prosthesis-specific negative contour of the customized patient-specific guide block with the corresponding contour of the first prosthetic component includes engaging a concave surface of the customized patient-specific guide block with a medial condyle surface of the femoral prosthetic component.

4. The method of claim 1, further comprising securing the alignment block to the cutting block, wherein engaging the alignment block with the guide pin includes advancing the cutting block along an anatomical axis of the bone to advance the alignment block into contact with the guide pin.

5. The method of claim 1, wherein the alignment block includes an indicator of a target joint line of a second prosthetic component.

6. The method of claim 1, further comprising assembling the customized patient-specific guide block by (i) locking a first removable drill bushing into a first hole of a customized patient-specific pin guide, and (ii) locking a second removable drill bushing into a second hole of the customized patient-specific pin guide.

7. The method of claim 1, wherein the cutting block includes a patient-universal cutting block having a distal cutting guide.

8. The method of claim 1, wherein engaging the alignment block with the guide pin to position the cutting block on the bone includes:

positioning the guide pin in a guide pin hole of the alignment block, advancing the alignment block into contact with the cutting block, engaging the cutting block with the bone, and aligning the cutting block with an indicator defined on the alignment block, the indicator corresponding to a target anterior-posterior position of the cutting block.

9. The method of claim 1, further comprising advancing a bone saw along a cutting guide surface of the customized patient-specific guide block when the customized patient-specific guide block is positioned on the first prosthetic component.

10. The method of claim 1, wherein attaching the customized patient-specific guide block to the first prosthetic component includes engaging a customized patient-specific negative contour shaped to match a corresponding contour of the bone of the patient with the bone of the patient, the customized patient-specific negative contour including a unique plurality of depressions and ridges that match a corresponding plurality of ridges and depressions of the corresponding contour of the bone of the patient.

* * * * *